(12) United States Patent
Fukuda

(10) Patent No.: US 11,643,658 B2
(45) Date of Patent: May 9, 2023

(54) OLIGONUCLEOTIDES, MANUFACTURING METHOD FOR SAME, AND TARGET RNA SITE-SPECIFIC EDITING METHOD

(71) Applicants: FUKUOKA UNIVERSITY, Fukuoka (JP); DAIICHI SANKYO COMPANY, LIMITED, Tokyo (JP)

(72) Inventor: Masatora Fukuda, Fukuoka (JP)

(73) Assignees: FUKUOKA UNIVERSITY, Fukuoka (JP); DAIICHI SANKYO COMPANY, LIMITED, Tokyo (JP)

( * ) Notice: Subject to any disclaimer, the term of this patent is extended or adjusted under 35 U.S.C. 154(b) by 0 days.

(21) Appl. No.: 16/770,161

(22) PCT Filed: Dec. 5, 2018

(86) PCT No.: PCT/JP2018/044751
§ 371 (c)(1),
(2) Date: Jun. 5, 2020

(87) PCT Pub. No.: WO2019/111957
PCT Pub. Date: Jun. 13, 2019

(65) Prior Publication Data
US 2020/0392496 A1    Dec. 17, 2020

(30) Foreign Application Priority Data

Dec. 6, 2017 (JP) ............................. JP2017-234341
Aug. 10, 2018 (JP) ............................. JP2018-151757

(51) Int. Cl.
*C12N 15/113* (2010.01)

(52) U.S. Cl.
CPC ...... *C12N 15/113* (2013.01); *C12N 2310/531* (2013.01)

(58) Field of Classification Search
CPC .................. C12N 15/113; C12N 2310/531
See application file for complete search history.

(56) References Cited

U.S. PATENT DOCUMENTS

2018/0208924 A1   7/2018   Fukuda et al.

FOREIGN PATENT DOCUMENTS

| WO | 2016/097212 | 6/2016 |
| WO | 2017/010556 | 1/2017 |

OTHER PUBLICATIONS

Fukuda et al. (Scientific Reports (Feb. 2, 2017) pp. 1-13). (Year: 2017).*
Montiel-Gonzalez et al. (Nucleic Acids Research (Aug. 23, 2016) e157, pp. 1-12 and supplemental pp. 1-38) (Year: 2016).*
International Search Report (ISR) dated Mar. 5, 2019 in International (PCT) Application No. PCT/JP2018/044751.

* cited by examiner

*Primary Examiner* — J. E. Angell
(74) *Attorney, Agent, or Firm* — Wenderoth, Lind & Ponack, L.L.P.

(57) ABSTRACT

Provided is a short-chain guide RNA that is able to induce site-specific editing even when only a small number of nucleotides is attached to the target recognition site. The guide RNA includes a first oligonucleotide that identifies the target RNA, and a second oligonucleotide that links to the 3' end of the first oligonucleotide. The first oligonucleotide contains: a target-corresponding nucleotide residue that corresponds to an adenosine residue in the target RNA; an oligonucleotide of 15 to 30 residues that links to the 5' end of the target-corresponding nucleotide residue and that has a base sequence complementary to the target RNA; and an oligonucleotide of 3 or 4 residues that links to the 3' end of the target-corresponding nucleotide residue and that has a base sequence complementary to the target RNA. The second oligonucleotide contains 2 to 24 nucleotide residues, and induces site-specific editing of the target RNA.

6 Claims, 6 Drawing Sheets

Specification includes a Sequence Listing.

del02

5AS-sADg_rdel02
SEQ ID NO: 49 del03

5AS-sADg_rdel03
SEQ ID NO: 50 del03.5

5AS-sADg_rdel03.5
SEQ ID NO: 51 del04

5AS-sADg_rdel04
SEQ ID NO: 52 del05

5AS-sADg_rdel05

OLIGONUCLEOTIDES, MANUFACTURING METHOD FOR SAME, AND TARGET RNA SITE-SPECIFIC EDITING METHOD

TECHNICAL FIELD

A sequence listing in electronic (ASCII text file) format is filed with this application and incorporated herein by reference. The name of the ASCII text file is "581571_CorrectedSequenceListing_20220329_ST25.txt"; the file was created on Apr. 18, 2022; the size of the file is 20.8 KB.

The present invention relates to oligonucleotides, a manufacturing method for the same, and a target RNA site-specific editing method.

BACKGROUND ART

In recent years, development of genome editing techniques is triggering the use of a method of controlling life phenomena by modifying genetic information that is a blueprint of organisms, i.e., DNA information in cells, as a disease treatment approach in the fields of medicine and drug discovery. Since DNA is a constant and invariable molecule in a cell, a DNA modification effect permanently remains in a target cell or a target organism. On the other hand, RNA is a nucleic acid molecule having DNA information copied therein and is a transient genetic information molecule repeatedly synthesized and degraded, unlike DNA. Therefore, modification of RNA information can provide a temporary non-permanent genetic information modification effect to a target organism. Thus, although an RNA modification technique is a gene modification technique like DNA modification, properties thereof are significantly different.

For example, WO 2016/097212 describes as an RNA modification technique an oligonucleotide construct for site-specific editing of nucleotides in a target RNA sequence, including a target-directional portion containing an antisense sequence complementary to a portion of a target RNA and a recruitment portion that can bind to and recruit an RNA editing entity present in a cell and capable of editing nucleotides. For example, WO 2017/010556 describes a site-specific RNA mutating method of causing double-strand-specific adenosine deaminase (ADAR) to act on a complex of a target RNA and a target editing guide RNA.

SUMMARY OF THE INVENTION

Problem to be Solved by the Invention

The oligonucleotide construct described in WO 2016/097212 has a stem loop structure having a specific repetitive sequence as a recruitment portion in addition to a target-directional site and requires 16 or more oligonucleotides for the recruitment portion. A target editing guide RNA described in WO 2017/010556 requires an ADAR binding region having a stem-loop structure consisting of a specific sequence of 40 or 49 residues in addition to an antisense region. Oligonucleotides applied to the RNA modification technique described in WO 2016/097212 or WO 2017/010556 essentially require an intramolecular double-stranded region having a certain length for binding to ADAR in addition to a site forming a double strand with a target RNA and therefore tends to inevitably have a longer overall length as oligonucleotides.

An object of the present invention is to provide a short-chain target editing guide RNA capable of inducing site-specific editing even when a small number of nucleotides is attached to a target recognition site.

Means for Solving Problem

Specific means for solving the problems are as follows, and the present invention includes the following aspects.

A first aspect provides oligonucleotides inducing site-specific editing of a target RNA including: a first oligonucleotide identifying the target RNA; and a second oligonucleotide linked to the 3' side of the first oligonucleotide, wherein the first oligonucleotide is composed of a target-corresponding nucleotide residue corresponding to an adenosine residue in the target RNA, an oligonucleotide of 15 to 30 residues linked to the 5' side of the target-corresponding nucleotide residue and having a base sequence complementary to the target RNA, and an oligonucleotide of 3 or 4 residues linked to the 3' side of the target-corresponding nucleotide residue and having a base sequence complementary to the target RNA, and wherein the second oligonucleotide is composed of 2 to 24 nucleotide residues.

A second aspect provides a target RNA site-specific editing method comprising: bringing a target RNA and oligonucleotides inducing site-specific editing of the target RNA into contact with each other in the presence of adenosine deaminase.

A third aspect provides a manufacturing method for oligonucleotides comprising: selecting a target RNA containing an adenosine residue that is an editing target; acquiring a first base sequence of 15 to 30 residues on the 3' side of the adenosine residue, a second base sequence of 3 or 4 residues on the 5' side of the adenosine residue, and a third base sequence of at least 2 residues adjacent to the 5' side of the second base sequence, included in the target RNA; and preparing an oligonucleotide in which an oligonucleotide having a base sequence complementary to the first base sequence, a target-corresponding nucleotide residue corresponding to the adenosine residue, an oligonucleotide having a base sequence complementary to the second base sequence, and an oligonucleotide having a base sequence complementary or non-complementary to the third base sequence are sequentially linked from the 5' side.

Effect of the Invention

The present invention can provide the short-chain target editing guide RNA capable of inducing site-specific editing even when a small number of nucleotides are attached to the target recognition site.

MODES FOR CARRYING OUT THE INVENTION

Figure 1:
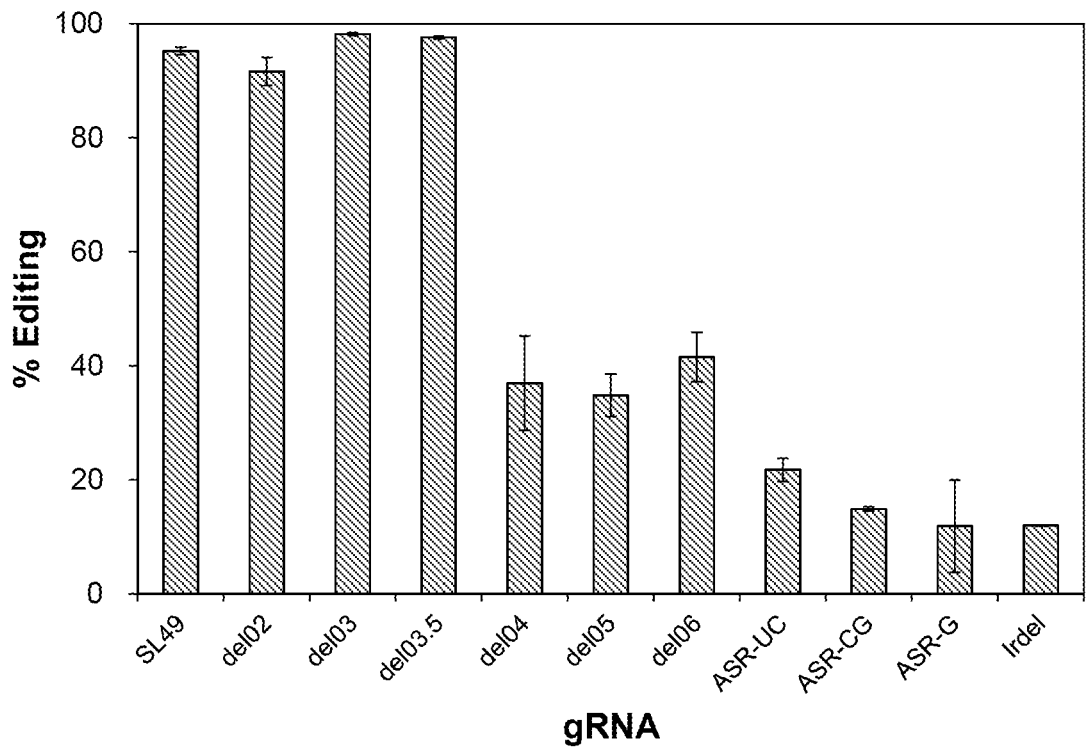
FIG. 1 is a view showing editing-inducing activity of target editing guide RNAs.

The term "step" as used herein comprises not only an independent step but also a step not clearly distinguishable from another step as long as the intended purpose of the step is achieved. If multiple substances correspond to a component in a composition, the content of the component in the composition means the total amount of the multiple substances present in the composition unless otherwise specified.

Target Editing Guide RNA

An oligonucleotide inducing site-specific editing of a target RNA (hereinafter, also referred to as a target editing guide RNA) contains a first oligonucleotide identifying the target RNA and a second oligonucleotide linked to the 3' side of the first oligonucleotide. The first oligonucleotide is composed of a target-corresponding nucleotide residue corresponding to an adenosine residue in the target RNA and corresponding to the adenosine residue, an oligonucleotide of 15 to 30 residues linked to the 5' side of the target-corresponding nucleotide residue and having a base sequence complementary to the target RNA, and an oligonucleotide of 3 or 4 residues linked to the 3' side of the target-corresponding nucleotide residue and having a base sequence complementary to the target RNA. The second oligonucleotide is composed of 2 to 24 nucleotide residues and has a base sequence complementary or non-complementary to a corresponding base sequence of the target RNA.

The target editing guide RNA has the short-chain second oligonucleotide having a sequence complementary or non-complementary to the corresponding base sequence of the target RNA on the 3' side of the first oligonucleotide identifying the target RNA, so that excellent site-specific editing may be induced. This is probably because, for example, ADAR catalyzing target editing recognizes a double-stranded region consisting of the target RNA and the first oligonucleotide and is enhanced in the editing activity by the second oligonucleotide that may be present in a state of being free from the target RNA without forming a double strand with the target RNA. Therefore, in the target editing guide RNA, the first oligonucleotide probably functions as a complementary region (antisense region; ASR) for the target RNA, and the second oligonucleotide probably functions as an editing enhancement region, an ADAR binding region (ADAR recruiting region; ARR), etc.

The target editing guide RNA of the present embodiment has a length shorter than a conventional target editing guide RNA, and accordingly, the manufacturing cost is simply reduced. Additionally, since chemical synthesis is facilitated, a method of directly introducing a chemically synthesized target editing guide RNA into a cell becomes easier in addition to a method of introducing the target editing guide RNA into a cell through gene expression. This also enables application of an existing artificial nucleic acid etc. used in nucleic acid medicine development etc. to the target editing guide RNA. As a result, an improvement in intracellular degradation resistance, an improvement in cell introduction efficiency, etc. make it possible to provide a further highly-functional target editing guide RNA. Furthermore, since the target editing guide RNA is made up of the minimum number of residues necessary for inducing editing, off-target editing may be suppressed at positions other than the adenosine residue that is the editing target while maintaining specificity to the target RNA.

For example, the target editing guide RNA recruits ADAR catalyzing target editing to the target RNA and thereby induces site-specific editing of the target RNA. ADAR is an enzyme converting an adenosine residue in double-stranded RNA into an inosine residue through a hydrolytic deamination reaction and is widely present in mammalian cells. Since the inosine residue has the structure similar to a guanosine residue, the RNA information is translated as a guanosine residue at the time of translation of the RNA information, and the RNA information is consequently edited. When such RNA editing occurs in a portion encoding an amino acid, amino acid substitution etc. occur even though no DNA mutation exists on the genome. ADAR1, ADAR2, and ADAR3 are known as ADAR in mammals and have different genes. The target editing guide RNA enhances the target editing activity of ADAR1 or ADAR2 among them.

When introduced into a mammalian cell, the target editing guide RNA can recruit ADAR present in the cell to the target RNA to induce the site-specific editing of the target RNA.

The first oligonucleotide contained in the target editing guide RNA identifies the target RNA. The target RNA is not particularly limited as long as the RNA contains an adenosine residue to be edited, may be either cellular RNA or viral RNA, and is usually pre-mRNA or mRNA encoding a protein. An editing site in the target RNA may be present in an untranslated region, a splice region, exon, intron, or any region affecting the stability, structure, or function of RNA. The target RNA may contain a mutation to be corrected or changed. Alternatively, the target RNA may have a sequence mutated to encode a phenotype different from a natural form.

The target RNA is preferably RNA encoding a protein, and specifically, examples of the encoded protein can include phosphorylated proteins related to signal transduction of serotonin receptors, glutamate receptors, membrane potential-dependent potassium channel, STAT3, NFkBIA, MAPK14 etc.

For example, the target editing guide RNAs can be applied to treatment of genetic diseases. Examples of the genetic diseases include cystic fibrosis, albinism, α-1 anti-trypsin deficiency, Alzheimer's disease, amyotrophic lateral sclerosis, asthma, β-thalassemia, CADASIL syndrome, Charcot-Marie-Tooth disease, chronic obstructive pulmonary disease (COPD), distal spinal muscular atrophy (DSMA), Duchenne/Becker muscular dystrophy, dystrophic epidermolysis bullosa, Epidermolysis bullosa, Fabry disease, Factor V Leiden-related disorders, familial adenoma, polyposis, galactosemia, Gaucher disease, glucose-6-phosphate dehydrogenase deficiency, hemophilia, hereditary hemochromatosis, Hunter syndrome, Huntington disease, Hurler syndrome, inflammatory bowel disease (IBD), hereditary polyagglutination syndrome, Leber congenital amaurosis, Lesch-nyhan syndrome, Lynch syndrome, Marfan syndrome, mucopolysaccharidosis, muscular dystrophy, myotonic dystrophy types I and II, neurofibromatosis, Niemann-Pick disease types A, B, and C, NY-eso-1-related pancreatic cancer, Parkinson's disease, Peutz-Jeghers syndrome, Phenylketonuria, Pompe disease, primary ciliary disease, prothrombin mutation-related disease such as prothrombin G20210A mutation, pulmonary hypertension, retinitis pigmentosa, Sandhoff disease, severe combined immunodeficiency syndrome (SCID), sickle cell anemia, spinal muscular atrophy, Stargardt disease, Tay-Sachs disease, Usher syndrome, X-linked immunodeficiency, various forms of cancer (e.g., BRCA1 and 2-related breast cancer and ovarian cancer).

The first oligonucleotide is composed of a target-corresponding nucleotide residue corresponding to an adenosine residue serving as an editing target in the target RNA and corresponding to the adenosine residue of the editing target, a 5'-side oligonucleotide of 15 to 30 residues linked to the 5' side of the target-corresponding nucleotide residue and having a base sequence complementary to a corresponding base sequence of the target RNA, and a 3'-side oligonucleotide of 3 or 4 residues linked to the 3' side of the target-corresponding nucleotide residue and having a base sequence complementary to a corresponding base sequence of the target RNA. The respective oligonucleotides linked to the 5' side and the 3' side of the target-corresponding nucleotide residue form a double strand with the target RNA, so that the target RNA and the editing target site in the target RNA are identified.

The target-corresponding nucleotide residue is a nucleotide residue corresponding to an adenosine residue serving as the editing target and is, for example, a cytidine residue, a uridine residue, an adenosine residue, or a derivative thereof. The target-corresponding nucleotide residue is preferably a base that does not form a base pair with an adenosine residue serving as the editing target, more preferably a cytidine residue or a derivative thereof, further preferably a cytidine residue.

The base sequence of the oligonucleotide linked to the 5' side or 3' side of the target-corresponding nucleotide residue is a base sequence complementary to the corresponding base sequence of the target RNA. The number of oligonucleotide residues linked on the 5' side of the target-corresponding nucleotide residue is, for example, 15 to 26 or 15 to 20 from the viewpoint of specificity to the target RNA. An additional sequence of about 1 to 6 residues controlling expression may separately be linked as needed to the 5' side of the oligonucleotide linked to the 5' side of the target-corresponding nucleotide residue. The number of the oligonucleotide residues linked to the 3' side of the target-corresponding nucleotide residue is preferably 3 from the viewpoint of editing activity.

The second oligonucleotide is composed of 2 to 24 nucleotide residues and has a base sequence complementary or non-complementary to the corresponding base sequence of the target RNA. Preferably, the second oligonucleotide does not form a base pair complementary to the target RNA and can be in a state of being free from the target RNA. Although the detailed mechanism is unknown, the presence of this free oligonucleotide chain probably contributes to the enhancement of the editing activity of ADAR. The second oligonucleotide preferably contains a guanosine residue linked adjacent to the target-corresponding nucleotide residue. Although the detailed reason is unknown, the editing activity of ADAR tends to be further enhanced when the second oligonucleotide is an oligonucleotide of two or more residues containing a guanosine residue linked adjacent to the target-corresponding nucleotide residue.

The second oligonucleotide (e.g., ARR) efficiently induces the site-specific editing when linked to the 3' side of the first oligonucleotide identifying the target RNA, while the ability to induce the site-specific editing is reduced in the case of being linked to the 5' side. In contrast, the conventional target editing guide RNA can induce the site-specific editing regardless of whether the ADAR binding region (ARR) is linked to the 3' side or the 5' side of the first oligonucleotide. Therefore, the target editing guide RNA according to the present embodiment is considered to be different from the conventional target editing guide RNA in the mechanism inducing the site-specific editing.

The number of residues of the second oligonucleotide is 2 or more and 24 or less, preferably 20 or less, more preferably 16 or less, further preferably 15 or less, particularly preferably 14 or less, and is, for example, 3 or more, 4 or more, 8 or more, 12 or more, or 13 or more. On the other hand, when the second oligonucleotide has a sequence complementary to the corresponding base sequence of the target RNA, the number of residues of the second oligonucleotide is 22 or less, for example.

When having a sequence non-complementary to the corresponding base sequence of the target RNA, the second oligonucleotide may have the non-complementary base sequence as a whole, and this does not exclude the second oligonucleotide containing nucleotide residues that may form a base pair complementary to the target RNA. For example, the content of the non-complementary base sequence in the base sequences of the second oligonucleotide and the corresponding target RNA is 50% or more, preferably 60% or more, more preferably 80% or more. This content of the non-complementary base sequence is calculated by dividing the number of nucleotide residues forming combinations of non-complementary bases in the corresponding base pairs by the number of residues of the second oligonucleotide.

When the second oligonucleotide has a sequence non-complementary to the corresponding base sequence of the target RNA, the base sequence of the second oligonucleotide may appropriately be selected depending on the corresponding base sequence of the target RNA etc. For example, when the corresponding base of the target RNA is a pyrimidine base, a purine residue or a pyrimidine base not forming a base pair may be selected as the corresponding base of the second oligonucleotide, which is preferably a pyrimidine base. When the corresponding base of the target RNA is a purine residue, a pyrimidine residue or a purine base not forming a base pair may be selected as the corresponding base of the second oligonucleotide, which is preferably a purine residue. Specifically, when the corresponding base of the target RNA is cytosine (C), cytosine (C), uracil (U), or adenine (A) may be selected as the corresponding base of the second oligonucleotide, which is preferably C or U. When the corresponding base of the target RNA is uracil (U), uracil (U), cytosine (C), or guanine (G) may be selected as the corresponding base of the second oligonucleotide, which is preferably U or C. When the corresponding base of the target RNA is adenine (A), adenine (A), guanine (G), or cytosine (C) may be selected as the corresponding base of the second oligonucleotide, which is preferably A or G. When the corresponding base of the target RNA is guanine (G), adenine (A), guanine (G), or uracil (U) may be selected as the corresponding base of the second oligonucleotide, which is preferably A or G. Specific examples of the second oligonucleotide having a sequence non-complementary to the corresponding base sequence of the target RNA include, for example, sequences comprising GGG, GG, GC, GA, GU, UC, UG, UA, UU, CG, CA, CU, CC, AG, AA, AC, AU, etc.

The second oligonucleotide may have a base sequence that may form a stem-loop structure in a molecule. When the target editing guide RNA has a stem-loop structure, the editing activity tends to be further enhanced. This is probably because, for example, when the second oligonucleotide forms a stem-loop structure, the free state from the target RNA becomes more stable. The stem-loop structure includes a stem portion forming a double strand of complementary base pairs in the molecule and a loop portion linking two oligonucleotides constituting the stem portion. The number of nucleotide residue pairs constituting the stem portion is, for example, 2 or more, preferably 3 or more, 4 or more, 5 or more, or 6 or more, and 10 or less, 9 or less, 8 or less, or 7 or less. The number of nucleotide residues constituting the loop portion is, for example, 4 or 5.

When the second oligonucleotide forms the stem-loop structure, the base sequence of the second oligonucleotide is not particularly limited as long as the stem-loop structure may be formed. However, the second oligonucleotide having a base sequence represented by (RY or YR) nNm (RY or YR)n is excluded. In this case, R is adenosine or guanosine, Y is uridine or cytidine, N is adenosine, guanosine, cytidine, uridine, or inosine, m is 3 or more, and n is 4 or more. The two base sequences represented by (RY)n or (YR)n form a double-stranded stem structure of complementary base pairs.

Specifically, for the base sequence of the second oligonucleotide forming the stem loop structure, the base sequence of the stem portion preferably contains guanine (G) and cytosine (C) from the viewpoint of the stability of the double-stranded structure. The proportion of G-C pairs in the base pairs of the stem portion is, for example, 60% or more, preferably 70% or more. Uracil (U) capable of forming a base pair with guanine (G) due to tautomerism may be included instead of cytosine (C).

From the viewpoint of target editing activity, the base sequence of the second oligonucleotide preferably contains at least one selected from the group consisting of a sequence composed of two or three consecutive guanines (GG or GGG), a sequence composed of consecutive uracil and guanine (UG), and a sequence composed of consecutive guanine, uracil, and guanine (GUG) in the 5'-side stem portion and contains a sequence capable of forming a complementary pair therewith (e.g., CC, CCC, CCU, CA, CAC) in the 3'-side stem portion. The base sequence also preferably contains a sequence consisting of guanine, uracil, and guanine continuous with the loop portion (GUG) in the 5'-side stem portion and contains a sequence capable of forming a complementary pair therewith (e.g., CAC) in the 3'-side stem portion.

For example, the loop portion of the second oligonucleotide may be any sequence of 4 or 5 residues. Specific examples of the sequence of the loop portion include, for example, GCUAA; a UNCG fold type such as UUCG, UACG, UGCG, UCCG; a GNRA fold type such as GAAA, GUAA, GCAA, GGAA, GAGA, GUGA, GCGA, GGGA; an RNYA fold type such as GUCA, GCCA, GGCA, GACA, AUCA, ACCA, AGCA, AACA, GUUA, GCUA, GGUA, GAUA, AUUA, ACUA, AGUA, AAUA; a GGUG fold type; a CUUG fold type; and an AGNN fold type such as AGUU, AGUC, AGUG, AGUA, AGCU, AGCC, AGCG, AGCA. For details of these loop structures, for example, Biophys. J., 113, 257-267, 2017 can be referred to.

Specific examples of the base sequence of the second oligonucleotide capable of forming the stem loop structure are shown below; however, the present invention is not limited thereto. Additionally, examples of the stem loop structure are shown in FIG. 2B.

TABLE 1

| | | |
|---|---|---|
| del02_ARR | GGGUGGAAUAUUCGUAU CCCACCU | SEQ ID NO: 49 |
| del03_ARR | GGGUGGUUCGCCACCU | SEQ ID NO: 50 |
| del03.5_ARR | GGGUGUUCGCACCU | SEQ ID NO: 51 |
| del04_ARR | GGGUUUCGACCU | SEQ ID NO: 52 |
| del05_ARR | GGUUCGCU | – |
| mut_loop | GGGUGGAAACACCU | SEQ ID NO: 53 |
| mut_GC | GGGUGGAAACACCC | SEQ ID NO: 54 |
| mut_all | UUCACGAAAGUGAA | SEQ ID NO: 55 |
| mut_1 | UGGUGGAAACACCA | SEQ ID NO: 56 |
| mut_2 | GUGUGGAAACACAC | SEQ ID NO: 57 |
| mut_3 | GGCUGGAAACAGCC | SEQ ID NO: 58 |
| mut_4 | GGGAGGAAACUCCC | SEQ ID NO: 59 |
| mut_5 | GGGUCGAAAGACCC | SEQ ID NO: 60 |
| mut_12 | UUGUGGAAACACAA | SEQ ID NO: 61 |
| mut_34 | GGCAGGAAACUGCC | SEQ ID NO: 62 |
| mut_345 | GGCACGAAAGUGCC | SEQ ID NO: 63 |

The nucleotide residues constituting the target editing guide RNA may be natural ribonucleotide residues or non-natural modified nucleotide residues. The modified nucleotide residues include those having a modified phosphodiester bond between nucleosides, those having a modified 2' hydroxy group of ribose, those having intramolecularly crosslinked ribose, those acquired by modifying at least one of purine and pyrimidine bases, etc. Examples of modification of the phosphodiester bond portion include, for example, phosphorothioation, methylphosphonation, methylthiophosphonation, phosphorodithioation, phosphoramidation, and peptide bond substitution. Examples of modification of the 2' hydroxy group of ribose include 2' methylation, 2'-O-methoxyethylation, 2'-O-aminopropylation (AP), 2'-fluorination, 2' methylcarbamoylethylation, 3,3-dimethylallylation, etc. Examples of the intramolecular cross-linked form of ribose include nucleotides in which the 2'-position and the 4'-position are cross-linked (2',4'-BNA). Examples of 2',4'-BNA include locked nucleic acid also referred to as LNA (α-L-methyleneoxy(4'-CH$_2$—O-2') BNA or β-D-methyleneoxy(4'-CH$_2$—O-2') BNA, ethyleneoxy(4'-(CH$_2$)$_2$—O-2') BNA also referred to as ENA), β-D-thio(4'-CH$_2$—S-2') BNA, aminooxy(4'-CH$_2$—O—N(R)-2') BNA (R is H or CH$_3$), oxyamino(4'-CH$_2$—N(R)—O-2') BNA (R is H or CH$_3$) also referred to as 2',4'-BNANC, 2',4'-BNA-COC, 3'amino-2',4'-BNA, 5'-methyl BNA, (4'-CH(CH$_3$)—O-2') BNA also referred to as cEt-BNA, (4'-CH(CH$_2$OCH$_3$)—O-2') BNA also referred to as cMOE-BNA, amide-type BNA (4'-C(O)—N(R)-2') BNA (R is H or CH$_3$) also referred to as AmNA, etc. Examples of modification of the base portion include halogenation; alkylation such as methylation, ethylation, n-propylation, isopropylation, cyclopropylation, n-butylation, isobutylation, s-butylation, t-butylation, and cyclobutylation; hydroxylation; amination; deamination; demethylation; etc.

Manufacturing Method for Target Editing Guide RNA

A manufacturing method for producing a target editing guide RNA includes: a selecting step of selecting a target RNA containing an adenosine residue that is an editing target; a base sequence acquisition step of acquiring a first base sequence of 15 to 30 residues on the 3' side of the adenosine residue, a second base sequence of 3 or 4 residues on the 5' side of the adenosine residue, and a third base sequence of at least 2 residues adjacent to the 5' side of the second base sequence, included in the target RNA; and a preparation step of preparing an oligonucleotide in which an oligonucleotide having a base sequence complementary to the first base sequence, a target-corresponding nucleotide residue corresponding to the adenosine residue, an oligonucleotide having a base sequence complementary to the second base sequence, and an oligonucleotide having a base sequence non-complementary to the third base sequence are sequentially linked from the 5' side.

At the target RNA selecting step, the target RNA containing an adenosine residue serving as an editing target is selected. The target RNA is selected from RNAs synthesized by a DNA-dependent RNA polymerase depending on the purpose of RNA editing etc. The target RNA may be any of mRNA transcribed from genomic DNA, mRNA without base modification, unspliced pre-mRNA, ncRNA, etc., and is preferably mRNA or pre-mRNA. The adenosine residue serving as an editing target may be present in any of untranslated regions, splice regions, exon regions, intron regions, or regions affecting the stability, structure, or function of RNA, depending on the purpose of RNA editing etc.

At the base sequence acquisition step, the base sequences of the selected target RNA are acquired. The acquired base sequences are the first base sequence corresponding to the oligonucleotide on the 3' side of the adenosine residue serving as the editing target, the second base sequence of 3 or 4 residues on the 5' side of the adenosine residue, and the third base sequence of at least 2 residues adjacent to the 5' side of the second base sequence. A sequence complementary to the first base sequence is the base sequence of the oligonucleotide linked to the 5' side of the target-corresponding nucleotide residue in the target editing guide RNA to be manufactured. A sequence acquired by linking a sequence complementary to the second base sequence and a sequence complementary or non-complementary to the third base sequence is the base sequence of the oligonucleotide linked to the 3' side of the target-corresponding nucleotide residue in the target editing guide RNA to be manufactured. Regarding the base sequence complementary or non-complementary to the third base sequence, the sequence can appropriately be selected with reference to the base sequence of the second oligonucleotide described above.

The number of nucleotide residues having bases identified as the first base sequence is 15 or more and 30 or less, preferably 15 or more and 26 or less, more preferably 15 or more and 20 or less. The number of nucleotide residues having bases identified as the second base sequence is 3 or 4, preferably 3. The number of nucleotide residues having bases identified as the third base sequence is 2 or more and, for example, 24 or less, preferably 20 or less, more preferably 16 or less, further preferably 15 or less, particularly preferably 14 or less.

The method for acquiring a base sequence is not particularly limited as long as the base sequence of the target oligonucleotide can be identified, and the method can appropriately be selected from commonly used techniques. For example, if the base sequence of the target RNA is known in a database etc., a base sequence of a necessary portion may be extracted and acquired from the known base sequence. Alternatively, the base sequence may be acquired by preparing a cDNA from the target RNA and determining the base sequence of the cDNA with a conventional method.

The preparation step includes preparing an oligonucleotide in which an oligonucleotide having a base sequence complementary to the first base sequence, a target-corresponding nucleotide residue corresponding to the adenosine residue, an oligonucleotide having a base sequence complementary to the second base sequence, and an oligonucleotide having a base sequence complementary or non-complementary to the third base sequence are sequentially linked from the 5' side. The oligonucleotide to be prepared serves as the target editing guide RNA comprising the first oligonucleotide identifying the target RNA and the second oligonucleotide linked to the 3' side of the first oligonucleotide.

An oligonucleotide having a predetermined base sequence can be manufactured by a known method. For example, the oligonucleotide can be prepared by using an appropriate synthetic oligo DNA with reference to the description in WO 2017/010556 etc. Alternatively, the oligonucleotide can be prepared by using a synthetic oligo DNA having a promoter sequence such as a T7 promoter on the 5' side of the base sequence of the target editing guide RNA. Furthermore, the oligonucleotide can be prepared in a chemosynthetic manner by a known manufacturing method such as a phosphoramidite method. The oligonucleotide can also be prepared by preparing a cDNA having a base sequence complementary to the oligonucleotide with a conventional method, constructing a plasmid DNA containing the acquired cDNA, and introducing the acquired plasmid DNA into an appropriate cell for transcription to RNA.

Target RNA Site-Specific Editing Method

A target RNA site-specific editing method includes bringing a target RNA into contact with a target editing guide RNA that is an oligonucleotide inducing site-specific editing of the target RNA, in the presence of adenosine deaminase. The target editing guide RNA can partially form a double strand with the target RNA and recruit adenosine deaminase so as to site-specifically convert an adenosine residue contained in the target RNA into an inosine residue.

For example, the target RNA site-specific editing method can be performed by introducing or expressing the target editing guide RNA described above into eukaryotic cells having the target RNA. A method of introducing the target editing guide RNA into eukaryotic cells can appropriately be selected and applied from various techniques used in nucleic acid medicine. By introducing a plasmid etc. capable of expressing the target editing guide RNA into eukaryotic cells, the target editing guide RNA can be expressed in eukaryotic cells.

By applying the target RNA site-specific editing method using the target editing guide RNA to mutation of amino acids related to functional expression of intracellular proteins such as a sugar chain modification site, a phosphorylation site, and a metal coordination site, a new methodology of temporarily controlling intracellular protein functions can be provided. By generalizing an in vivo protein function controlling method according to the target RNA site-specific editing method using the target editing guide RNA, a molecular technology contributable to development of researches in the life science field can be achieved.

Nucleic acid medicine is conventionally developed by utilizing suppression of target protein expression with siRNA or target protein function control with functional RNA called aptamer. However, medicine converting information of mRNA to modify the function of the target protein encoded by mRNA is unprecedented. Therefore, the target editing guide RNA has the potential to create a novel nucleic acid medicine showing unprecedented efficacy.

For example, a nonsense mutation hereditary disease is a disease caused by absence of synthesis of an original protein due to a stop codon formed by a point mutation on a gene. Examples of the nonsense mutation hereditary disease may comprise muscular dystrophy, multiple sclerosis, Alzheimer's disease, nerve tissue degeneration, neurological diseases such as Parkinson's disease, and cancer. For example, the target editing guide RNA may probably be used for a nucleic acid medicine editing stop codons such as UAA, UAG, and UGA, etc. and thereby achieving an unprecedented mechanism for the diseases described above. Specifically, for example, protein synthesis may be controlled by editing the stop codon UAG into the tryptophan codon UIG.

For example, for many proteins have important functions in cells, ON/OFF of functions is precisely controlled through phosphorylation/dephosphorylation, and it has been suggested that abnormalities in phosphorylation/dephosphorylation is deeply involved in various diseases including cancer. Examples of a phosphorylation site of protein include Tyr, Thr, and Ser. By editing the codons encoding these amino acids into codons encoding other amino acids by the target editing guide RNA, the phosphorylation of protein can be suppressed. Specifically, for example, the phosphorylation of intracellular protein can be controlled by editing the Tyr codon UAC into the Cys codon UIC.

EXAMPLES

The present invention will hereinafter more specifically be described with reference to examples; however, the present invention is not limited to these examples.

Reference Example 1

Preparation of Model Target RNA

GFP-Gq-TK Plasmid was used as a template for amplification by PCR (1 cycle (98° C. for 10 seconds, 55° C. for 30 seconds, 68° C. for 30 seconds) in a reaction solution containing 10 μM AcGFP_sRNA02 T7F01 primer, 10 μM AcGFP_sRNA02 R01 primer, 2.5 mM dNTP, 1.25 U/μL Prime Star GXL (Takara Bio Inc.) (final concentration: GFP-Gq-TK Plasmid, 4.0 pg/μL; AcGFP_sRNA02 T7 F/R, 0.3 μM; dNTP 0.2 mM; and PrimeStar GXL, 0.025U/μL). The amplified PCR product was subjected to phenol/chloroform extraction and ethanol precipitation to purify DNA. The acquired DNA was used as a template to synthesize RNA through in vitro transcription (37° C., 3 hours) by using T7-Scribe Standard RNA IVT KIT (manufactured by CELLSCRIPT). Subsequently, DNase (final concentration: 0.05 U/μL) was added for treatment (37° C., 15 minutes), and RNA was purified through phenol/chloroform extraction and ethanol precipitation. The acquired RNA was purified by 8M Urea PAGE (8%), extracted by grinding and immersion, and purified by a 0.22 μm filter (manufactured by DURAPORE) and gel filtration (manufactured by BIO RAD) to prepare a model target RNA (sGFP) having 160 nt residues. Table 2 shows the primers used and the sequence of the acquired model target RNA.

TABLE 2

| | | |
|---|---|---|
| AcGFP_sRNA02_T7F01 | CTAATACGACTCACTATAGGG TGAATGGCCACAAGTTCAG | SEQ ID NO: 1 |
| AcGFP_sRNA02_R01 | TAGCGTGAGAAGCACTGCAC | SEQ ID NO: 2 |
| sGFP | CTAATACGACTCACTATAGGG TGAATGGCCACAAGTTCAGCG TGAGCGGCGAGGGCGAGGGCG ATGCCACCTACGGCAAGCTGA CCCTGAAGTTCATCTGCACCA CCGGCAAGCTGCCTGTGCCCT GGCCCACCCTGGTGACCACCC TGAGCTACGGCGTGCAGTGCT TCTCACGCTA | SEQ ID NO: 3 |

Example 1

Preparation of Target Editing Guide RNA

A reaction solution containing 100 μM of synthetic oligo DNA (F) (gRNA3r_T7F) and 100 μM of synthetic oligo DNA (R) (gRNA3r_del02) was treated at 95° C. for 3 minutes and then cooled for treatment at 25° C. for 15 minutes for an annealing reaction to acquire DNA (gRNA3r_del02F/R) with only the T7 promoter region forming a double strand. Subsequently, 2.5 mM dNTP and 5000 U/mL Klenow fragment were added (final concentration: gRNA3r_del02F/R, 2 μM; dNTP, 0.2 mM; and Klenow fragment 0.025 U/μl) for elongation at 25° C. for 30 minutes, and DNA was purified through phenol/chloroform extraction and ethanol precipitation. The acquired DNA was used as a template to synthesize RNA (target editing guide RNA) through in vitro transcription (37° C., 3 hours) by using T7-Scribe Standard RNA IVT KIT (manufactured by CELLSCRIPT). Subsequently, DNase (final concentration: 2 U) was added for treatment at 37° C. for 15 minutes, and RNA was purified through phenol/chloroform extraction and ethanol precipitation. The acquired RNA was purified by 8M Urea PAGE (8%), extracted by grinding and immersion, and purified by a 0.22 μm filter (manufactured by DURAPORE) and gel filtration (manufactured by BIO RAD) to prepare the intended target editing guide RNA (del02). Table 3 shows the sequence of the synthetic oligo DNA used, and Table 4 shows the sequence of the acquired target editing guide RNA. Table 6 shows only the ADAR binding region (ARR; the second oligonucleotide) of the target editing guide RNA.

Examples 2 to 9

The target editing guide RNAs of Examples 2 to 9 were acquired as in Example 1 except that synthetic oligo DNAs (R) shown in Table 3 were used as the synthetic oligo DNA (R). Table 4 shows the sequences of the acquired target editing guide RNAs. Table 6 shows only the ADAR binding regions (ARR; the second oligonucleotides) of the target editing guide RNAs.

Comparative Examples 1 and 2

Target editing guide RNAs of Comparative Examples 1, 2 were acquired as in Example 1 except that synthetic oligo DNAs (R) shown in Table 3 were used. Table 4 shows the sequences of the acquired target editing guide RNAs.

Reference Example 2

With reference to the description of Example 1 in WO 2017/010556, a conventional target editing guide RNA (hereinafter, also referred to as SL49) was prepared such that the ADAR binding region composed of 49 residues forming the stem loop structure is linked to the 3' side of the antisense region RNA. Specifically, the target editing guide RNA of Reference Example 2 was acquired by using gRNA3r_Glu_T7F as a synthetic oligo DNA (1) and gRNA3r_Glu_conseq_R as a synthetic oligo DNA (2). Table 5 shows the sequences of the synthetic oligo DNAs used and the sequence of the acquired target editing guide RNA (SL49).

TABLE 5

| gRNAD3r_Glu_T7F | CTAATACGACTCACTATAGGG AAGCACTGCACGCCGCAGCGG GTGGAATAG | SEQ ID NO: 27 |
| --- | --- | --- |
| gRNAD3r_Glu_conseq_R | AGGTGGGATACTATAACAACA TTTAGCATATTGTTATACTAT TCCACCC | SEQ ID NO: 28 |

TABLE 3

| Example 1 | gRNA3r_del02 | AGGTGGGATACGAATATTCCACCCGCTGCGGCGTGCAGTGCTTCCCTATAGTGAGTCGTATTAG | SEQ ID NO: 4 |
| --- | --- | --- | --- |
| Example 2 | gRNA3r_del03 | AGGTGGCGAACCACCCGCTGCGGCGTGCAGTGCTTCCCTATAGTGAGTCGTATTAG | SEQ ID NO: 5 |
| Example 3 | gRNA3r_del03.5 | AGGTGCGAACACCCGCTGCGGCGTGCAGTGCTTCCCTATAGTGAGTCGTATTAG | SEQ ID NO: 6 |
| Example 4 | gRNA3r_del04 | AGGTCGAAACCCGCTGCGGCGTGCAGTGCTTCCCTATAGTGAGTCGTATTAG | SEQ ID NO: 7 |
| Example 5 | gRNA3r_del05 | AGCGAACCGCTGCGGCGTGCAGTGCTTCCCTATAGTGAGTCGTATTAG | SEQ ID NO: 8 |
| Example 6 | gRNA3r_del06 | CCGCTGCGGCGTGCAGTGCTTCCCTATAGTGAGTCGTATTAG | SEQ ID NO: 9 |
| Example 7 | gRNA3r_GGG | CCCGCTGCGGCGTGCAGTGCTTCCCTATAGTGAGTCGTATTAG | SEQ ID NO: 10 |
| Example 8 | gRNA3r_UC | GAGCTGCGGCGTGCAGTGCTTCCCTATAGTGAGTCGTATTAG | SEQ ID NO: 11 |
| Example 9 | gRNA3r_CG | CGGCTGCGGCGTGCAGTGCTTCCCTATAGTGAGTCGTATTAG | SEQ ID NO: 12 |
| Comparative Example 1 | gRNA3r_Irde1 | GCTGCGGCGTGCAGTGCTTCCCTATAGTGAGTCGTATTAG | SEQ ID NO: 13 |
| Comparative Example 2 | gRNA3r_G | CGCTGCGGCGTGCAGTGCTTCCCTATAGTGAGTCGTATTAG | SEQ ID NO: 14 |
| — | gRNA3r_T7F | CTAATACGACTCACTATAGGG | SEQ ID NO: 15 |

TABLE 4

| Example 1 | del02 | GGGAAGCACUGCACGCCGCAGCGGGUGGAAUAUUCGUAUCCCACCU | SEQ ID NO: 16 |
| --- | --- | --- | --- |
| Example 2 | del03 | GGGAAGCACUGCACGCCGCAGCGGGUGGUUCGCCACCU | SEQ ID NO: 17 |
| Example 3 | del03.5 | GGGAAGCACUGCACGCCGCAGCGGGUGUUCGCACCU | SEQ ID NO: 18 |
| Example 4 | del04 | GGGAAGCACUGCACGCCGCAGCGGGUUUCGACCU | SEQ ID NO: 19 |
| Example 5 | del05 | GGGAAGCACUGCACGCCGCAGCGGUUCGCU | SEQ ID NO: 20 |
| Example 6 | del06 | GGGAAGCACUGCACGCCGCAGCGG | SEQ ID NO: 21 |
| Example 7 | ASR-GGG | GGGAAGCACUGCACGCCGCAGCGGG | SEQ ID NO: 22 |
| Example 8 | ASR-UC | GGGAAGCACUGCACGCCGCAGCUC | SEQ ID NO: 23 |
| Example 9 | ASR-CG | GGGAAGCACUGCACGCCGCAGCCG | SEQ ID NO: 24 |
| Comparative Example 1 | Irdel | GGGAAGCACUGCACGCCGCAGC | SEQ ID NO: 25 |
| Comparative Example 2 | ASR-G | GGGAAGCACUGCACGCCGCAGCG | SEQ ID NO: 26 |

TABLE 5-continued

| | |
|---|---|
| SL49 | GGGAAGCACUGCACGCCGCAG CCGGGUGGAAUAGUAUAACAA UAUGCUAAAUGUUGUUAUAGU AUCCCACCU   SEQ ID NO: 29 |

TABLE 6

| | | | |
|---|---|---|---|
| Example 1 | del02 | GGGUGGAAUAUUCG UAUCCCACCU | SEQ ID NO: 49 |
| Example 2 | del03 | GGGUGGUUCGCCAC CU | SEQ ID NO: 50 |
| Example 3 | del03.5 | GGGUGUUCGCACCU | SEQ ID NO: 51 |
| Example 4 | del04 | GGGUUUCGACCU | SEQ ID NO: 52 |
| Example 5 | del05 | GGUUCGCU | — |
| Example 6 | del06 | GG | — |
| Example 7 | ASR-GGG | GGG | — |
| Example 8 | ASR-UC | UC | — |
| Example 9 | ASR-CG | CG | — |

Evaluation 1

The editing-inducing activity of the target editing guide RNA prepared as described above was evaluated in vitro by using the model target RNA. First, the model target RNA and the target editing guide RNA were subjected to an annealing reaction to form a complex, and purified recombinant hADAR2 was added for an editing reaction. To analyze the editing efficiency of the target site, cDNA of the target RNA was amplified by RT-PCR, and an editing percentage was calculated from a chromatogram acquired from direct sequencing. The specific protocol is as follows.

Evaluation of Editing Inducibility of Target Editing Guide RNA (gRNA) (In Vitro)

In annealing buffer (150 mM NaCl, 10 mM Tris-HCl (pH 7.6)), 0.3 µM model target RNA and 0.9 µM gRNA are thermally denatured (80° C., 3 minutes) and cooled for 15 minutes to 25° C. for the annealing reaction. The editing reaction of 5 nM RNA complex and 12.5 nM hADAR2 was conducted at 37° C. for 1 hour in an editing reaction buffer (20 mM HEPES-KOH [pH 7.5], 100 mM NaCl, 2 mM $MgCl_2$, 0.5 mM DTT, 0.01% Triton X-100, 5% glycerol, 1 U/µL Murine RNase Inhibitor (manufactured by New England BioLabs). After the reaction, RNA was purified through phenol/chloroform extraction and ethanol precipitation and dissolved with 5 µL of TE buffer. A recovered RNA sample was subjected to a reverse transcription reaction using PrimeScript Reverse Transcriptase II (manufactured by TaKaRa) to synthesize cDNA. The acquired cDNA was used as a template to amplify dsDNA by PCR using a 0.3 µM T7GFP_sRNA_F01 primer and a 0.3 µM GFP_sRNA_R01 primer. Big Dye Terminator v3.1 Cycle Sequencing Kit was used for direct sequencing of dsDNA amplified with the 0.165 µM T7proGGG primer. Finally, the editing percentage (%) was calculated from a peak height ratio G/(G+A) of the acquired chromatogram. The results are shown in Table 8 and FIG. 1.

TABLE 7

| | | |
|---|---|---|
| T7GFP_sRNA_F01 | CTAATACGACTCACTATAGGG TGAATGGCCACAAGTTCAG | SEQ ID NO: 64 |
| GFP_sRNA_R01 | TAGCGTGAGAAGCACTGCAC | SEQ ID NO: 65 |
| T7proGGG | CTAATACGACTCACTATAGGG | SEQ ID NO: 46 |

TABLE 8

| | Editing rate (%) | |
|---|---|---|
| gRNA | Average (n = 3) | Standard Deviation (n = 3) |
| SL49 | 95.2 | 0.7 |
| del02 | 91.6 | 2.4 |
| del03 | 98.2 | 0.3 |
| del03.5 | 97.6 | 0.2 |
| del04 | 36.9 | 8.3 |
| del05 | 34.8 | 3.8 |
| del06 | 41.5 | 4.3 |
| ASR-UC | 21.8 | 2.0 |
| ASR-CG | 14.9 | 0.4 |
| ASR-G | 11.9 | 8.1 |
| Irdel | 12.0 | 0.1 |

The target editing guide RNAs (gRNA) del02, del03, and del03.5 showed the editing-inducing activity comparable to the conventional form (SL49). The target editing guide RNA (gRNA) having any two residues added to the 3' side of the antisense region (ASR) showed the enhanced editing-inducing activity as compared to Irdel having substantially only the antisense region. Particularly, the target editing guide RNA (del06) having two consecutive guanosine residues adjacent to the 3' side of ASR showed the enhanced editing-inducing activity.

Figure 2A:
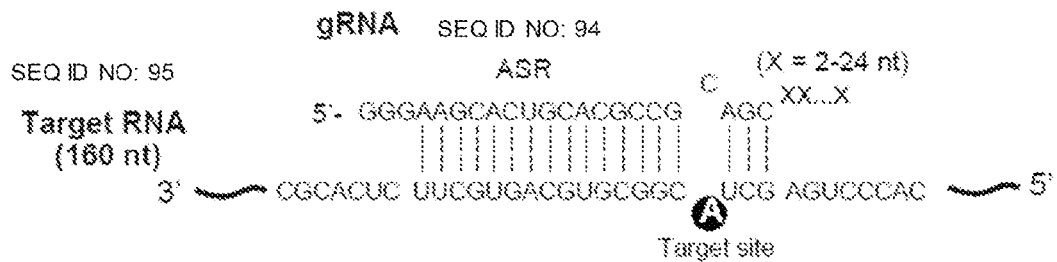
FIG. 2A is a schematic diagram showing an example of a complex of a target editing guide RNA and a target RNA.
Figure 2B:
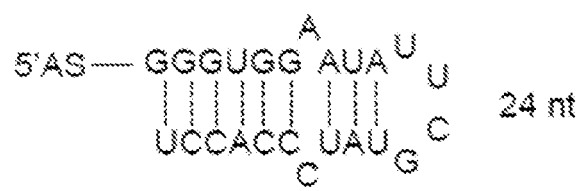
FIG. 2B is a schematic diagram showing an example of a structure of the target editing guide RNA.
Figure 2B:
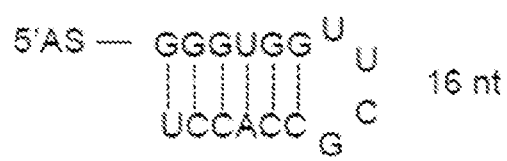
Figure 2B:
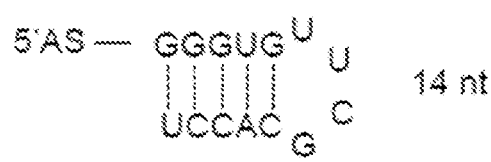
Figure 2B:
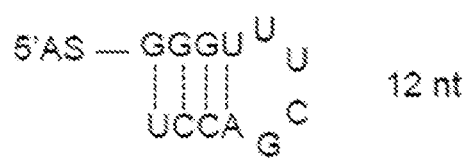
Figure 2B:
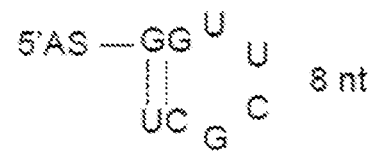

For example, the target editing guide RNA is considered to form a complex with a target RNA (Target RNA) such that a double strand is partially formed as shown in FIG. 2A. In the complex of FIG. 2A, a first oligonucleotide portion functions as the antisense region (ASR) to form a double strand with the target RNA, and the second nucleotide linked to the 3' side of the first oligonucleotide is present in a present in a from state in terms of the target RNA. Particularly, when the second nucleotide is a short chain of up to about 4 residues, the free state is probably be achieved due to thermal fluctuation even if the second nucleotide has a sequence complementary to the corresponding base sequence of the target RNA. This free state is considered to allow the second oligonucleotide portion to function as an editing enhancement region. It is noted that since the synthetic oligo DNA (F) used for preparing the target editing guide RNA had an additional sequence GGG for regulating expression added to the 3' side of the T7 promoter, GGG was added to the 5' end of the target editing guide RNA.

The second oligonucleotide of the target editing guide RNA may form a stem-loop structure in the molecule as shown in FIG. 2B. For example, when the number of residues of the second oligonucleotide is 14 or more, a more stable stem-loop structure is formed, so that the editing activity is probably further improved.

Evaluation 2

The editing-inducing activity of the target editing guide RNA in cultured cells then was verified by using an editing fluorescent reporter (GFP_W58X). In GFP_W58X serving as the target RNA, the codon (UGG) of Trp58 of wild-type (WT) GFP is mutated to a stop codon (UAG). Therefore, mature GFP is not directly expressed; however, the adenosine residue of the stop codon is edited at the RNA level into the inosine residue, and the inosine residue is translated as the guanosine residue, so that mature GFP is expressed. The specific protocol is as follows.

Reference Example 3

Construction of Substrate GFP_W58X Expression Plasmid

A plasmid acquired by cloning AcGFP in a pUC19 vector, i.e., a pUC19-GFP-TK plasmid, was used as a template to produce a 5'-side template DNA by PCR using a 0.3 μM AcGFP_XhoI_kozF01 primer, a 0.3 μM AcGFP_W58X_R01 primer, and PrimeStar GXL DNA Polymerase. The PCR conditions were 98° C./10 seconds, 55° C./15 seconds, 68° C./20 seconds, and 30 cycles. The pUC19-GFP-TK plasmid was then used as a template to produce a 3'-side template DNA by PCR using a 0.3 μM AcGFP_W58X_F01 primer, a 0.3 μM AcGFP_RNA_HindIII_R01 primer, and PrimeStar GXL DNA Polymerase. The PCR conditions were 98° C./10 seconds, 55° C./15 seconds, 68° C./40 seconds, and 30 cycles. For each of Samples diluted 100 times, a template DNA was prepared by PCR using the 0.3 μM AcGFP_XhoI_kozF01 primer, the 0.3 μM AcGFP_RNA_HindIII_R01 primer, and PrimeStar GXL DNA Polymerase. The PCR conditions were 98° C./10 seconds, 55° C./15 seconds, 68° C./60 seconds, and 30 cycles. The acquired template DNA and pcDNA3.1 (−) Hygro were subjected to a restriction enzyme treatment with XhoI and HindIII at 37° C. for 1 hour. The molar ratio of vector:plasmid was set to 1:5 by using DNA Ligation Kit (manufactured by TaKaRa), and a Ligation reaction was performed at 16° C. for 30 minutes. After Ligation, 2 μL of the solution was added to 20 μL of E. coli DH5α competent cells (manufactured by TaKaRa) for transformation, and the cells were cultured in an LB agar medium containing 50 μg/mL ampicillin at 37° C. for a day and a night. ExTaq (manufactured by TaKaRa) was used for performing insert check through colony PCR (a 0.3 μM pcDNA3_1pro_F01 primer, a 0.3 μM pcDNA3_1-seqR01 primer, 98° C./10 seconds, 55° C./30 seconds, 72° C./30 seconds, 30 cycles). Subsequently, a liquid medium was used for culturing a colony in which a plasmid was transformed by insertion of an insert, and the plasmid was extracted. Finally, base sequence analysis was performed by using Big Dye Terminator, a 0.165 μM pcDNA3_1pro_F01 primer, and a 0.165 μM pcDNA3_1-seqR01 primer, and it was confirmed that the inserted insert had a correct sequence. As described above, a plasmid (pcDNA3.1 (−) Hygro-AcGFPW58X) expressing GFP_W58X serving as a substrate RNA was constructed. Table 9 shows the sequences of the primers used for the construction.

TABLE 9

| AcGFP_XhoI_kozF01 | GCATGCTCGAGGGGCCGA TGGTGAGC | SEQ ID NO: 30 |
|---|---|---|
| AcGFP_W58X_R01 | CAGGGTGGGCTAGGGCAC AGG | SEQ ID NO: 31 |

TABLE 9-continued

| AcGFP_W58X_F01 | CCTGTGCCCTAGCCCACCC TG | SEQ ID NO: 32 |
|---|---|---|
| AcGFP_RNA_HindIII_R01 | GGTACAAGCTTTCACTTGT ACAGCTCATCCA | SEQ ID NO: 33 |
| pcDNA3_1pro_F01 | TGGCACCAAAATCAACGGG | SEQ ID NO: 34 |
| pcDNA3_1-seqR01 | GCTATTGTCTTCCCAATCC TCC | SEQ ID NO: 35 |

Example 10

Construction of Short-Chained 5AS-shADg_GFP173 Expression Plasmid

After an annealing reaction of 2 μM ADgrGFP173_del3_BglF and ADgrGFP173_del3_HindR (95° C., 3 minutes, slope to 25° C./15 minutes), an elongation reaction was performed using 0.2 mM dNTP and Klenow fragment (25° C., 30 minutes). A template DNA was purified through phenol/chloroform extraction and ethanol precipitation. The template DNA and pSuper-neo were subjected to a restriction enzyme treatment with BglII and HindIII (37° C., 1 hour). The molar ratio of vector:plasmid was set to 1:5 by using DNA Ligation Kit (manufactured by TaKaRa), and a Ligation reaction was performed at 16° C. for 30 minutes. After Ligation, 2 μL of the solution was added to 20 μL of E. coli DH5α competent cells (manufactured by TaKaRa) for transformation, and the cells were cultured in an LB agar medium containing 50 μg/mL ampicillin (at 37° C. for a day and a night). ExTaq (manufactured by TaKaRa) was used for performing insert check through colony PCR (0.3 μM pSuper.neo-InsCheck_F01 primer, a 0.3 μM pSuper.neo-InsCheck_R01 primer, 98° C./10 seconds, 55° C./30 seconds, 72° C./30 seconds, 30 cycles). Subsequently, a liquid medium was used for culturing a colony in which a plasmid was transformed by insertion of an insert, and the plasmid was extracted. Finally, base sequence analysis was performed by using Big Dye Terminator, a 0.165 μM pSuper.neo-InsCheck_F01 primer, and a 0.165 μM pSuperneo-InsCheck_R01 primer, and it was confirmed that the inserted insert had a correct sequence. Table 10 shows the sequences of the primers used for plasmid construction. The acquired plasmid expresses a target editing guide RNA (5AS-shADg_GFP173) corresponding to the target editing guide RNA (del03) of Example 2.

Example 11

Construction of Short-Chain ADg_rGFP_del035 Expression Plasmid

A plasmid was constructed as in Example 10 except that grGFP173_del35_BglF and grGFP173_del35_HindR were used as primers. Table 10 shows the sequences of the primers used. The acquired plasmid (pSuper_ADg_rGFP_del03.5) expresses a target editing guide RNA (ADg_rGFP_del035) corresponding to the target editing guide RNA (del03.5) of Example 3.

Reference Example 4

Construction of Conventional 5AS-ADg_GFP173 Expression Plasmid

A plasmid (pSuper_neo_5AS-ADg_GFP173) was constructed as in Example 10 except that gR3rminiGW58X_BglF and gRNA3rminiU5_HindR01 were used as primers. Table 10 shows the sequences of the primers used. The acquired plasmid expresses a target editing guide RNA (5AS-ADg_rGFP173) corresponding to the target editing guide RNA (SL49) of Reference Example 2.

TABLE 10

| | | |
|---|---|---|
| ADgrGFP173_del3_BglF | CTAAGATCTGTCACCAGGGTGGGCCAGGGGGTGGTTC | SEQ ID NO: 36 |
| ADgrGFP173_del3_HindR | CTAAAGCTTAAAAAGGTGGCGAACCACCCCCTGGCCC | SEQ ID NO: 37 |
| pSuper.neo-InsCheck_F01 | CTGGGAAATCACCATAAACGTG | SEQ ID NO: 38 |
| pSuper.neo-InsCheck_R01 | CAGCTATGACCATGATTACGC | SEQ ID NO: 39 |
| grGFPA173_del35_BglF | CTAAGATCTGTCACCAGGGTGGGCCAGGGGGTGTTCGC | SEQ ID NO: 40 |
| grGFPA173_del35_HinR | CTAAAGCTTAAAAAGGTGCGAACACCCCCTGGCCC | SEQ ID NO: 41 |
| gR3rminiGW58X_BglF | GCTATAGATCTGTCACCAGGGTGGGCCAGGGGGTGGAATAGTATAC | SEQ ID NO: 42 |
| gRNA3rminiU5_HindR01 | CCGATAAGCTTAAAAAGGTGGGATACTATACCACGAATGGTATACTATTCCACCC | SEQ ID NO: 43 |

A plasmid (pcDNA3.1 (−) Hygro hADAR2) expressing human adenosine deaminase 2 (hADAR2) was constructed as follows.

Reference Example 5

Construction of pcDNA3.1 (−) Hygro_HisADAR2

With pYES/NT_A_ADAR2 used as a template, PCR was performed by using a 0.25 µM HisADAR2_XbaF01 primer and a 0.25 µM HisADAR2_KpnR01 primer under the condition of the extension reaction of 2 minutes. The insert was amplified by PCR. The insert and pcDNA3.1 (−) Hygro were subjected to an enzyme reaction using XbaI and KpnI at 37° C. for 1 hour. After purification through phenol/chloroform extraction and ethanol precipitation, 2 µL was added to 20 µL of E. coli DH5α competent cells (TaKaRa) for transformation, and the cells were cultured overnight in LB ampicillin agar medium. The generated colony was used as a template to perform PCR using a 0.3 µM T7proGGG primer and a 0.3 µM BGH reverse primer under the condition of the elongation reaction of 2 minutes for insert check before liquid culture of a clone having an amplification product with an intended fragment length. The sequence of the extracted plasmid was subjected to a sequencing reaction with Big Dye Terminator v3.1 Cycle Sequencing Kit (ABI) using a 0.165 µM M T7proGGG primer, a 0.165 µM BGH reverse primer, and a 0.165 µM HisADAR2_seqfw primer for base sequence analysis. Table 11 shows the sequences of the primers used.

TABLE 11

| | | |
|---|---|---|
| HisADAR2_XbaF01 | GCTCTAGAACCATGGGGGGTTCTATC | SEQ ID NO: 44 |
| HisADAR2_KpnR01 | GATGGTACCTCAGGGCGTGAGTGAG | SEQ ID NO: 45 |
| T7proGGG | CTAATACGACTCCACTATAGGG | SEQ ID NO: 46 |
| BGH reverse | TAGAAGGCACAGTCGAGG | SEQ ID NO: 47 |

TABLE 11-continued

| | | |
|---|---|---|
| HisADAR2_seqfw | GACCTCAGCTTGTCTGCTTC | SEQ ID NO: 48 |

Evaluation of Intracellular Editing Inducibility of Target Editing Guide RNA (gRNA) 1

Figure 3:
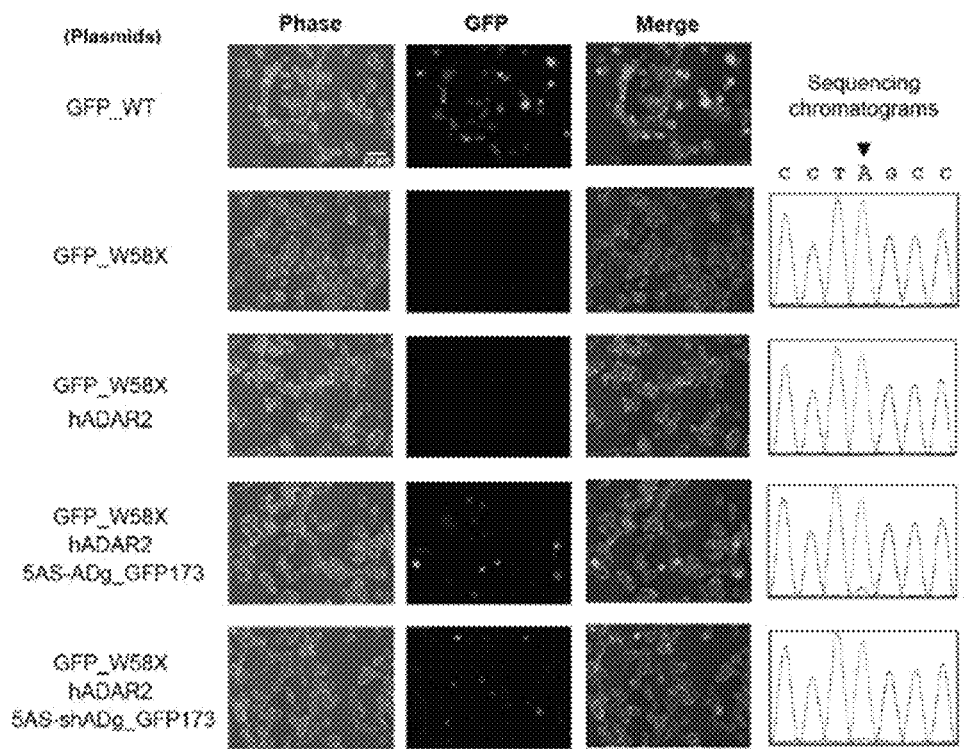
FIG. 3 is a view showing the editing-inducing activity of the target editing guide RNA in cells.

HEK293 cells were seeded on a 35 mm glass dish at 1.6×10$^5$ cells/well and cultured for 48 hours. Subsequently, 700 ng of ADAR2 expression plasmid (pcDNA3.1 (−) Hygro_His-ADAR2), 700 ng of substrate RNA expression plasmid (pcDNA3.1 (−) Hygro_AcGFPW58X), and 700 ng of gRNA expression plasmid (PSuper_neo_5AS-ADg_GFP173 or pSuper_neo_5AS-shADg_GFP173) were transduced by using X-tremeGENE HP DNA Transfection Reagent (Roche) and cultured for 72 hours. After removal of the medium and replacement with D-PBS (−), observation was performed with a confocal fluorescence microscope. The results are shown in FIG. 3. Phase of FIG. 3 is the result of phase difference observation, GFP is the result of fluorescence observation, and Merge is a combination thereof.

The editing efficiency was analyzed as follows. After recovering the cells, total RNA was extracted using 1000 µL of Sepasol RNA I Super G (manufactured by Nacalai), a DNase treatment was performed by using 10 U of Recombinant DNase I, and RNA was purified through phenol/chloroform extraction and ethanol precipitation in the presence of sodium acetate. A reverse transcription reaction using Transcriptor First Strand cDNA Synthesis Kit (manufactured by Roche), 0.5 µg of Total RNA, and 0.25 µM Oligo (dT) 17 was performed (denaturation: 80° C., 3 minutes, heat-chill; annealing: 65° C., 10 minutes; elongation: 55° C., 30 minutes; heat treatment: 85° C., 5 minutes) to amplify cDNA. AcGFP fragments were amplified by performing a first PCR for 60 seconds of elongation using 0.25 U Prime-Star GXL DNA polymerase, a 0.25 µM AcGFP_RNAf_T7F01 primer, and a 0.25 µM 3'-ADP primer and a second PCR for 60 seconds of elongation using a 0.25 µM AcGFP_RNAf_T7F01 primer and a 0.25 µM AcGFP-RNAfR01 primer. A sequencing reaction was performed for 60 seconds of elongation using Big Dye Terminator v3.1 Cycle Sequencing Kit (manufactured by ABI) and a 0.165 µM AcGFP_RNAf_T7F01 primer to acquire chromatograms. The chromatograms (Sequencing chromatograms) are also shown in FIG. 3.

Evaluation of Intracellular Editing Inducibility of Target Editing Guide RNA (gRNA) 2

Figure 4:
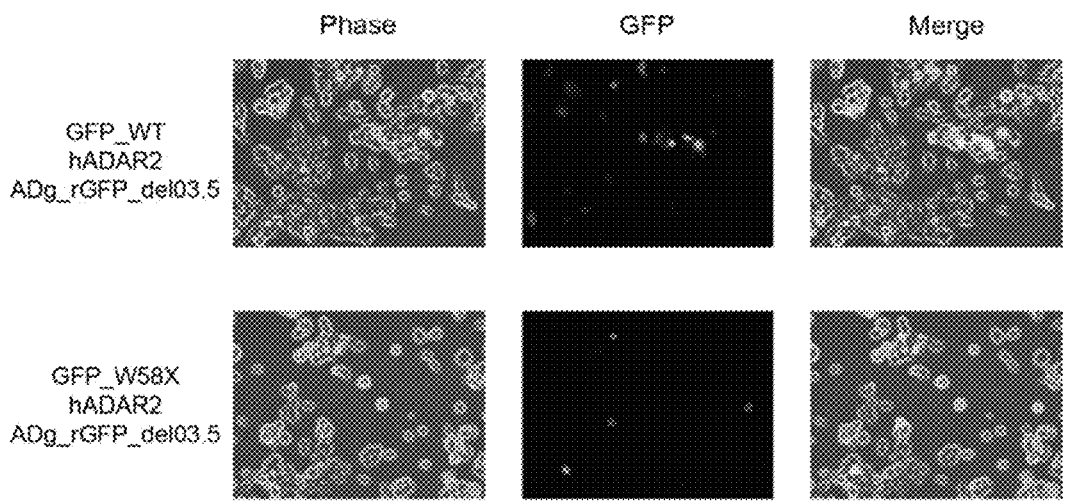
FIG. 4 is a view showing the editing-inducing activity of the target editing guide RNA in cells.

The intracellular editing inducibility was evaluated as described above, except that pSuper_ADg_rGFP_del03.5 acquired in Example 11 was used as the gRNA expression plasmid. The result is shown in FIG. 4.

From FIG. 3, no cells emitting fluorescence were observed in cells expressing only GFP_W58X or only GFP_W58X and hADAR2. On the other hand, transduction of the AD-gRNA expression plasmid into these cells resulted in confirmation of a large number of cells emitting fluorescence, i.e., expressing GFP. Furthermore, from the chromatogram acquired by direct sequencing of the extracted GFP_W58X, it was confirmed that A173 was edited in an AD-gRNA-dependent manner. It is noted that GFP_WT of FIG. 3 is a system in which mRNA of wild-type GFP was expressed. In FIG. 4, even when the number of residues of the second oligonucleotide was reduced to 14 residues, the same level of editing activity as the conventional target editing guide RNA was exhibited.

Examples 12 to 22

Figure 5:
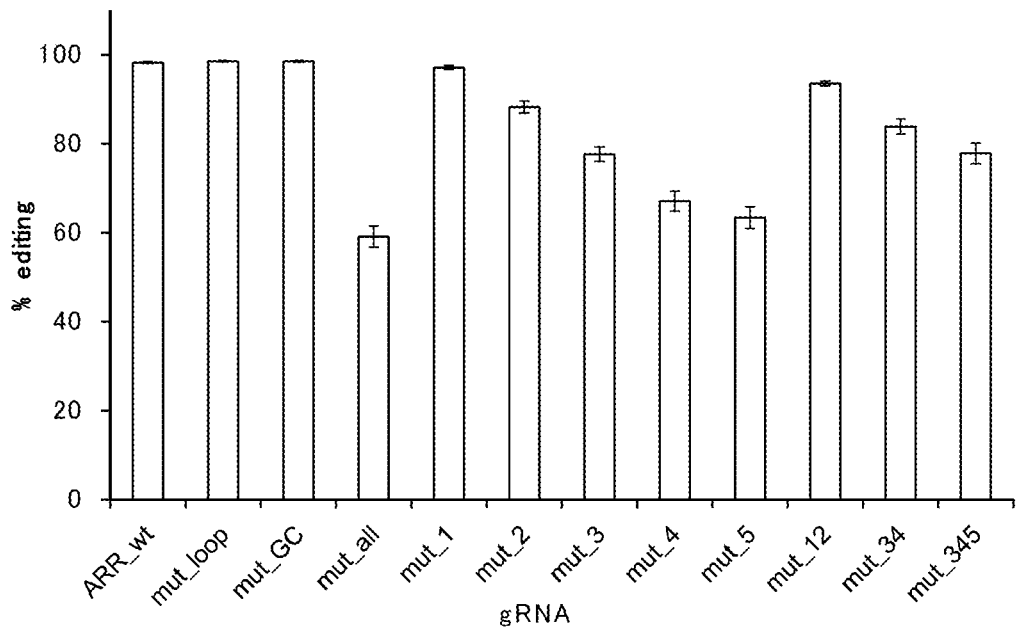
FIG. 5 is a view showing the editing-inducing activity of target editing guide RNAs different in sequence of an ADAR binding region.

Target editing guide RNAs with the second oligonucleotide (ARR) having the base sequences shown in Table 12 were prepared according to the method described in Example 1. The editing-inducing activities of the acquired target editing guide RNAs were evaluated together with the target editing guide RNA (ARR_wt) acquired in Example 3 in the same manner as Evaluation 1 described above. The results are shown in Table 13 and FIG. 5.

TABLE 12

| Example 3 | ARR_wt | GGGUGUUCGCACCU | SEQ ID NO: 66 |
| Example 12 | mut_loop | GGGUGGAAACACCU | SEQ ID NO: 53 |
| Example 13 | mut_GC | GGGUGGAAACACCC | SEQ ID NO: 54 |
| Example 14 | mut_all | UUCACGAAAGUGAA | SEQ ID NO: 55 |
| Example 15 | mut_1 | UGGUGGAAACACCA | SEQ ID NO: 56 |
| Example 16 | mut_2 | GUGUGGAAACACAC | SEQ ID NO: 57 |
| Example 17 | mut_3 | GGCUGGAAACAGCC | SEQ ID NO: 58 |
| Example 18 | mut_4 | GGGAGGAAACUCCC | SEQ ID NO: 59 |
| Example 19 | mut_5 | GGGUCGAAAGACCC | SEQ ID NO: 60 |
| Example 20 | mut_12 | UUGUGGAAACACAA | SEQ ID NO: 61 |
| Example 21 | mut_34 | GGCAGGAAACUGCC | SEQ ID NO: 62 |
| Example 22 | mut_345 | GGCACGAAAGUGCC | SEQ ID NO: 63 |

TABLE 13

| | Editing rate (%) | |
|---|---|---|
| gRNA | Average (n = 3) | Standard Deviation (n = 3) |
| ARR_wt | 98.3 | 0.20 |
| mut_loop | 98.6 | 0.15 |
| mut_GC | 98.5 | 0.16 |
| mut_all | 59.2 | 2.37 |
| mut_1 | 97.2 | 0.48 |
| mut_2 | 88.3 | 1.34 |
| mut_3 | 77.7 | 1.61 |
| mut_4 | 67.1 | 2.27 |
| mut_5 | 63.4 | 2.43 |
| mut_12 | 93.5 | 0.55 |
| mut_34 | 83.9 | 1.69 |
| mut_345 | 77.8 | 2.33 |

Figure 6:
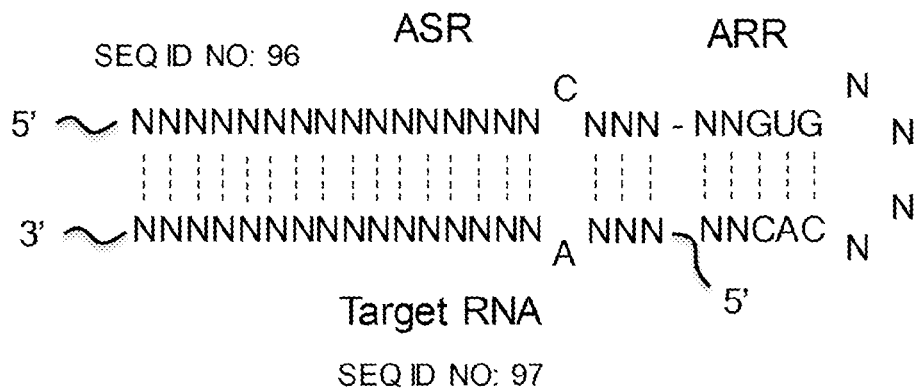
FIG. 6 is a schematic diagram showing an example of the structure of the target editing guide RNA.

As described above, in a preferred embodiment of the target editing guide RNA, the first oligonucleotide has an oligonucleotide of 15 to 30 residues having a base sequence complementary to the corresponding base sequence of the target RNA on the 5' side of the target-corresponding nucleotide residue (e.g., C) and an oligonucleotide of 3 residues having a base sequence complementary to the corresponding base sequence of the target RNA on the 3' side of the target-corresponding nucleotide residue, and the second oligonucleotide contains an arbitrary sequence (NN) as a stem portion on the 5' side and a sequence (GUG) consisting of consecutive guanine, uracil, and guanine and contains a sequence capable of forming a complementary pair with the 5'-side stem portion in the 3'-side stem portion via a loop portion consisting of an arbitrary sequence of 4 residues. This editing guide RNA is schematically represented in FIG. 6, for example.

Example 23

Luciferase Reporter Aassay

Dual-Luciferase Reporter Assay System (manufactured by Promega) was used for confirming the editing-inducing activity of endogenous ADAR as follows. For a reporter expression plasmid, psiCHECK2_Rluc_K41R_W104X was constructed. The psiCHECK2_Rluc_K41R_W104X was acquired from a commercially available psiCHECK (registered trademark) -2 (manufactured by Promega) by converting 104W (tryptophan) in the region encoding Renilla luciferase (Rluc) into 104X (stop codon) and 41K (lysine) into 41R (arginine). Specifically, an editing target was set by mutating 311G corresponding to the 104th tryptophan to 311A. Additionally, 41K is a site edited by ADAR independently of the target editing guide RNA and is converted into 41R; however, it is confirmed that this mutation has no effect on luminescence measurement. The sequence of the target RNA (Rluc W104X) is shown in Table 14.

For a target editing guide RNA expression plasmid, pSuper_shADg_Rluc_A311 was constructed. The pSuper_shADg_Rluc_A311 targets 311A for editing and expresses a target editing guide RNA (shADg_Rluc_A311) having the same sequence of 14 residues as Example 3 as the ADAR binding region (ARR; the second oligonucleotide). For a control, pSuper_shADg_Rluc_A311 was constructed as a plasmid expressing only the antisense region (ASR; the first oligonucleotide; 5AS_Rluc_A311). The sequences of RNAs expressed by the plasmids are shown in Table 14.

TABLE 14

| | | |
|---|---|---|
| shADg_Rluc_A311 | GAAGGUUCAGCAGCUCGAACCAAGGGGUGUUCGCACCUU | SEQ ID NO: 67 |
| 5AS_Rluc_A311 | GAAGGUUCAGCAGCUCGAACCAAG | SEQ ID NO: 68 |
| Rluc_W104X | AUGGCUUCCAAGGUGUACGACCCCGAGCAACGCAAACGCAUGAUCACUGGGCCU<br>CAGUGGUGGGCUCGCUGCAAGCAAAUGAACGUGCUGGACUCCUUCAUCAACUAC<br>UAUGAUUCCGAGAGGCACGCCGAGAACGCCGUGAUUUUUCUGCAUGGUAACGCU<br>GCCUCCAGCUACCUGUGGAGGCACGUCUGCCUCACAUCGAGCCCGUGGCUAGA<br>UGCAUCAUCCCUGAUCUGAUCGGAAUGGGUAAGUCCGGCAAGAGCGGGAAUGGC<br>UCAUAUCGCCUCCUGGAUCACUACAAGUACCUCACCGCUUAGUUCGAGCUGCUG<br>AACCUUCCAAAGAAAAUCAUCUUUGUGGGCCACGACUGGGGGGCUUGUCUGGCC<br>UUUCACUACUCCUACGAGCACCAAGACAAGAUCAAGGCCAUCGUCCAUGCUGAG<br>AGUGUCGUGGACGUGAUCGAGUCCUGGGACGAGUGGCCUGACAUCGAGGAGGAU<br>AUCGCCCUGAUCAAGAGCGAAGAGGGCGAGAAAAUGGUGCUUGAGAAUAACUUC<br>UUCGUCGAGACCAUGCUCCCAAGCAAGAUCAUGCGGAAACUGGAGCCUGAGGAG<br>UUCGCUGCCUACCUGGAGCCAUUCAAGGAGAAGGGCGAGGUUAGACGGCCUACC<br>CUCUCCUGGCCUCGCGAGAUCCCUCUCGUUAAGGGAGGCAAGCCCGACGUCGUC<br>CAGAUUGUCCGCAACUACAACGCCUACCUUCGGGCCAGCGACGAUCUGCCUAAG<br>AUGUUCAUCGAGUCCGACCCUGGGUUCUUUUCCAACGCUAUUGUCGAGGGAGCU<br>AAGAAGUUCCCUAACACCGAGUUCGUGAAGGUGAAGGGCCUCCACUUCAGCCAG<br>GAGGACGCUCCAGAUGAAAUGGGUAAGUACAUCAAGAGCUUCGUGGAGCGCGUG<br>CUGAAGAACGAGCAGUAA | SEQ ID NO: 69 |

Tet-ADAR2 cells capable of controlling the expression of human ADAR2 were subcultured on a 24-well Plate at 8.0×10⁴ cells/well and cultured in a medium containing 5.0 μg/mL of Dox for 48 hours. With FuGENE HP Transfection Reagent (manufactured by Roche), 15 ng of psiCHECK2_Rluc_K41R_W104X and 500 ng of pSuper_shADg_Rluc_A311 (the target editing guide RNA expression plasmid) or pSuper_5AS_Rluc_A311 (the plasmid expressing only the antisense region) were transfected and cultured in a medium containing 5.0 μg/mL of Dox for 72 hours. The Tet-ADAR2 cells are described in RNA, 18, 1735-1744 (2012).

A cell extract was acquired from the cultured cells by using 100 μL of Passive Lysis Buffer (manufactured by Promega). After 60 seconds from addition of 100 μL of LARII to 20 μL of the acquired cell extract, the luminescence intensity of Fluc was measured by GloMax (registered trademark) 20/20 Luminometer (manufactured by Promega). Subsequently, 100 μL of Stop & Glo Reagent was added, and after 60 seconds, the luminescence intensity of Rluc was measured. The luminescence intensity of Rluc normalized by the luminescence intensity of Fluc is shown in FIG. 7.

Figure 7:
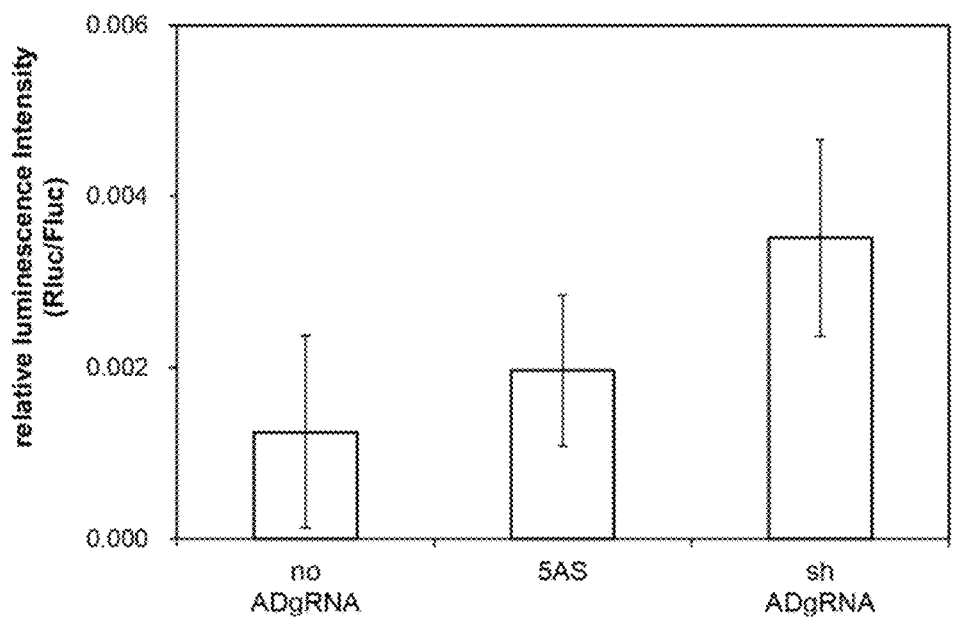
FIG. 7 is a view showing the editing-inducing activity of the target editing guide RNA in cells expressing hADAR.

As shown in FIG. 7, the expression of the target editing guide RNA (shADg_Rluc_A311) having 14 residues of ARR resulted in the editing of the target RNA with endogenous hADAR2.

A difference in target editing activity was studied as follows in terms of the antisense regions contained on the 5' side and on the 3' side of the ADAR binding region.

Example 24

Figure 8:
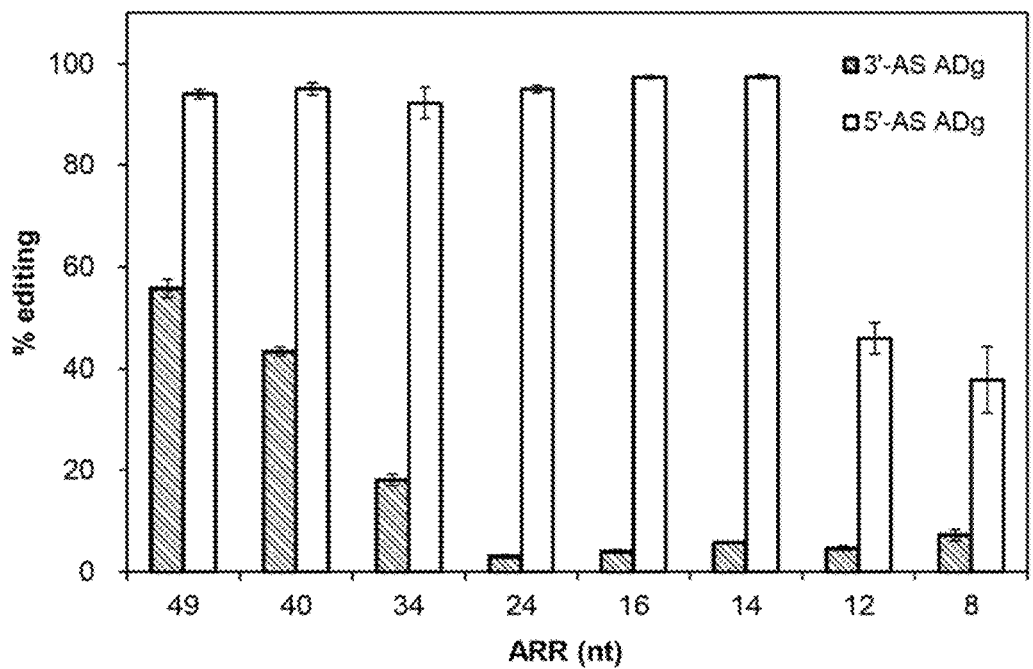
FIG. 8 is a view showing the relationship between the number of residues in an ADAR binding region and the editing-inducing activity.

In addition to the target editing guide RNAs (5'-AS ADg) having the antisense regions (ASR; the first oligonucleotide) acquired in Examples 1 to 5 and Reference Example 2 on the 5' side of the ADAR binding region (ARR; the second oligonucleotide; underlined in the table), the target editing guide RNAs (3'-AS ADg) having the antisense regions (ASR) of Examples 1 to 5 and Reference Example 2 on the 3' side of the ADAR binding region (ARR; underlined in the table) were prepared as described above. The sequences of the prepared target editing guide RNAs are shown in Table 15. Additionally, a target editing guide RNA having ASR on the 5' side or 3' side of ARR of 40 residues and 34 residues was prepared as described above. The editing-inducing activities of the prepared target editing guide RNAs were evaluated in the same manner as Evaluation 1 described above. The results are shown in FIG. 8.

TABLE 15

| | | |
|---|---|---|
| 3'-AS ADg-GFP_A200 49-ARR | GGGUGGAAUAGUAUAACAAUAUGCUAAAUGUUGUUAUAGUAUCCCACCUGCGCAGGCGUGCAGUGC<br>UUCUC | SEQ ID NO: 70 |
| 3'-AS ADg-GFP_A200 40-ARR | GGGUGGAAUAGUAUACCAUUCGUGGUAUAGUAUCCCACCUGCGCAGGCGUGCAGUGCUUCUC | SEQ ID NO: 71 |
| 3'-AS ADg-GFP_A200 34-ARR | GGGUGGAAUAGUAUAUUCGUAUAGUAUCCCACCUGCGCAGGCGUGCAGUGCUUCUC | SEQ ID NO: 72 |
| 3'-AS ADg-GFP_A200 24-ARR | GGGUGGAAUAUUCGUAUCCCACCUGCGCAGGCGUGCAGUGCUU | SEQ ID NO: 73 |
| 3'-AS ADg-GFP_A200 16-ARR | GGGUGGUUCGCCACCUGCGCAGGCGUGCAGUGCUU | SEQ ID NO: 74 |
| 3'-AS ADg-GFP_A200 14-ARR | GGGUGUUCGCACCUGCGCAGGCGUGCAGUGCUU | SEQ ID NO: 75 |
| 3'-AS ADg-GFP_A200 12-ARR | GGGUUUCGACCUGCGCAGGCGUGCAGUGCUU | SEQ ID |

TABLE 15-continued

| | | | |
|---|---|---|---|
| | | | NO: 76 |
| 3'-AS ADg-GFP_A200 8-ARR | GGG<u>UUCGCUG</u>CGCAGGCGUGCAGUGCUU | | SEQ ID NO: 77 |
| 5'-AS ADg-GFP_A200 49-ARR | GGGAAGCACUGCACGCCGCAGC<u>GGGUGGAAUAGUAUAACAAUAUGCUAAAUGUUGUUAUAGUAUCCCACCU</u> | | SEQ ID NO: 29 |
| 5'-AS ADg-GFP_A200 40-ARR | GGGAAGCACUGCACGCCGCAGC<u>GGGUGGAAUAGUAUACCAUUCGUGGUAUAGUAUCCCACCU</u> | | SEQ ID NO: 78 |
| 5'-AS ADg-GFP_A200 34-ARR | GGGAAGCACUGCACGCCGCAGC<u>GGGUGGAAUAGUAUAUUCGUAUAGUAUCCCACCU</u> | | SEQ ID NO: 79 |
| 5'-AS ADg-GFP_A200 24-ARR | GGGAAGCACUGCACGCCGCAGC<u>GGGUGGAAUAUUCGUAUCCCACCU</u> | | SEQ ID NO: 16 |
| 5'-AS ADg-GFP_A200 16-ARR | GGGAAGCACUGCACGCCGCAGC<u>GGGUGGUUCGCCACCU</u> | | SEQ ID NO: 17 |
| 5'-AS ADg-GFP_A200 14-ARR | GGGAAGCACUGCACGCCGCAGC<u>GGGUGUUCGCACCU</u> | | SEQ ID NO: 18 |
| 5'-AS ADg-GFP_A200 12-ARR | GGGAAGCACUGCACGCCGCAGC<u>GGGUUUCGACCU</u> | | SEQ ID NO: 19 |
| 5'-AS ADg-GFP_A200 8-ARR | GGGAAGCACUGCACGCCGCAGC<u>GGUUCGCU</u> | | SEQ ID NO: 20 |

From FIG. 8, the target editing guide RNAs with ARR having the number of residues of 49 (Reference Example 2), 40, and 34 are recognized to have favorable editing-inducing activity in both the 5'-AS type (5'-AS ADg) and the 3'-AS type (3'-AS ADg). On the other hand, the target editing guide RNAs with ARR having the number of residues of 24 or less (corresponding to Examples 1 to 5) exhibits favorable editing-inducing activity only in the 5'-AS type and does not exhibit sufficient editing-inducing activity in the 3'-AS type. This probably indicates that, for example, the 5'-AS type and 3'-AS type target editing guide RNAs are different in the mechanism inducing the editing activity of ADAR.

The editing position selectivity of the target editing guide RNA having short-chain ARR was evaluated as follows.

Example 25

Evaluation of Editing Position Selectivity

Based on sGFP RNA, target RNAs were designed and synthesized such that A serving as an editing target was arranged at a set position, according to the following method.

AAA (middle A corresponds to GFP A200) was introduced into the target RNA for evaluating the selectivity for one base before and after the target (−1, 1).

UAUAUAU was introduced into the target RNA for evaluating the selectivity for two bases before and after the target.

The target RNA used for evaluating the selectivity for positions three bases or more away from the target was prepared by fixing and arranging a sequence of UAC at a position away from the target so that the bases before and after the sequence does not change. For example, UAC-UACCGUAC was introduced as a target sequence for evaluation of 3 and 8.

The sequences of the target RNAs are shown in Table 16 with the target portion underlined. It is noted that sGFP_sR-NA_AAA is the target RNA for evaluating the position selectivity for 1 base before and after the target; sGFP_sR-NA_UAU is the target RNA for evaluating the selectivity for positions 2 bases away before and after the target; sGFP_sRNA_3.8 is the target RNA for evaluating the selectivity for positions 3 and 8 bases away from the target; sGFP_sRNA_4.9 is the target RNA for evaluating the selectivity for positions 4 and 9 bases away from the target; sGFP_sRNA_5.10 is the target RNA for evaluating the selectivity for positions 5 and 10 bases away from the target; sGFP_sRNA_6.11 is the target RNA for evaluating the selectivity for positions 6 and 11 bases away from the target; and sGFP_sRNA_7.12 is the target RNA for evaluating the selectivity for positions 7 and 12 bases away from the target.

TABLE 16

| | | |
|---|---|---|
| sGFP_sRNA_AAA | GGGUGAAUGGCCACAAGUUCAGCGUGAGCGGCGAGGGCGAGGGCGAUGCCACCUA<br>CGGCAAGCUGACCCUGAAGUUCAUCUGCACCACCGGCAAGCUGCCUGUGCCCUGG<br>CCCACCCUGGUGACCACCCUGAGC<u>AAA</u>GGCGUGCAGUGCUUCUC | SEQ ID NO: 80 |
| sGFP_sRNA_UAU | GGGUGAAUGGCCACAAGUUCAGCGUGAGCGGCGAGGGCGAGGGCGAUGCCACCUA<br>CGGCAAGCUGACCCUGAAGUUCAUCUGCACCACCGGCAAGCUGCCUGUGCCCUGG<br>CCCACCCUGGUGACCACCCUGA<u>UAUAUAU</u>CGUGCAGUGCUUCUCACGCUA | SEQ ID NO: 81 |
| sGFP_sRNA_3.8 | GGGUGAAUGGCCACAAGUUCAGCGUGAGCGGCGAGGGCGAGGGCGAUGCCACCUA<br>CGGCAAGCUGACCCUGAAGUUCAUCUGCACCACCGGCAAGCUGCCUGUGCCCUGG<br>CCCACCCUGGUGACCACCCUGAGCUACGGCGUGCAGUGCUUCUCACGCUACGC<u>UA</u><br>CGUU<u>ACUAC</u>CGU<u>AC</u>GGGCGUGCUGAAGAACGAGCAGUAA | SEQ ID NO: 82 |

TABLE 16-continued

| | | |
|---|---|---|
| sGFP_sRNA_4.9 | GGGUGAAUGGCCACAAGUUCAGCGUGAGCGGCGAGGGCGAGGGCGAUGCCACCUA CGGCAAGCUGACCCUGAAGUUCAUCUGCACCACCGGCAAGCUGCCUGUGCCCUGG CCCACCCUGGUGACCACCCUGAGCUACGGCGUGCAGUGCUUCUCACGCUACGCUA CGUUACGUACCGUACGGCGUGCUGAAGAACGAGCAGUAA | SEQ ID NO: 83 |
| sGFP_sRNA_5.10 | GGGUGAAUGGCCACAAGUUCAGCGUGAGCGGCGAGGGCGAGGGCGAUGCCACCUA CGGCAAGCUGACCCUGAAGUUCAUCUGCACCACCGGCAAGCUGCCUGUGCCCUGG CCCACCCUGGUGACCACCCUGAGCUACGGCGUGCAGUGCUUCUCACGCUACGCUA CGUUACGGUACCGUACGCGUGCUGAAGAACGAGCAGUAA | SEQ ID NO: 84 |
| sGFP_sRNA_6.11 | GGGUGAAUGGCCACAAGUUCAGCGUGAGCGGCGAGGGCGAGGGCGAUGCCACCUA CGGCAAGCUGACCCUGAAGUUCAUCUGCACCACCGGCAAGCUGCCUGUGCCCUGG CCCACCCUGGUGACCACCCUGAGCUACGGCGUGCAGUGCUUCUCACGCUACGCUA CGUUACGGGUACCGUACCGUGCUGAAGAACGAGCAGUAA | SEQ ID NO: 85 |
| sGFP_sRNA_7.12 | GGGUGAAUGGCCACAAGUUCAGCGUGAGCGGCGAGGGCGAGGGCGAUGCCACCUA CGGCAAGCUGACCCUGAAGUUCAUCUGCACCACCGGCAAGCUGCCUGUGCCCUGG CCCACCCUGGUGACCACCCUGAGCUACGGCGUGCAGUGCUUCUCACGCUACGCUA CGUUACCGGGUACCGUACGUGCUGAAGAACGAGCAGUAA | SEQ ID NO: 86 |

Figure 9:
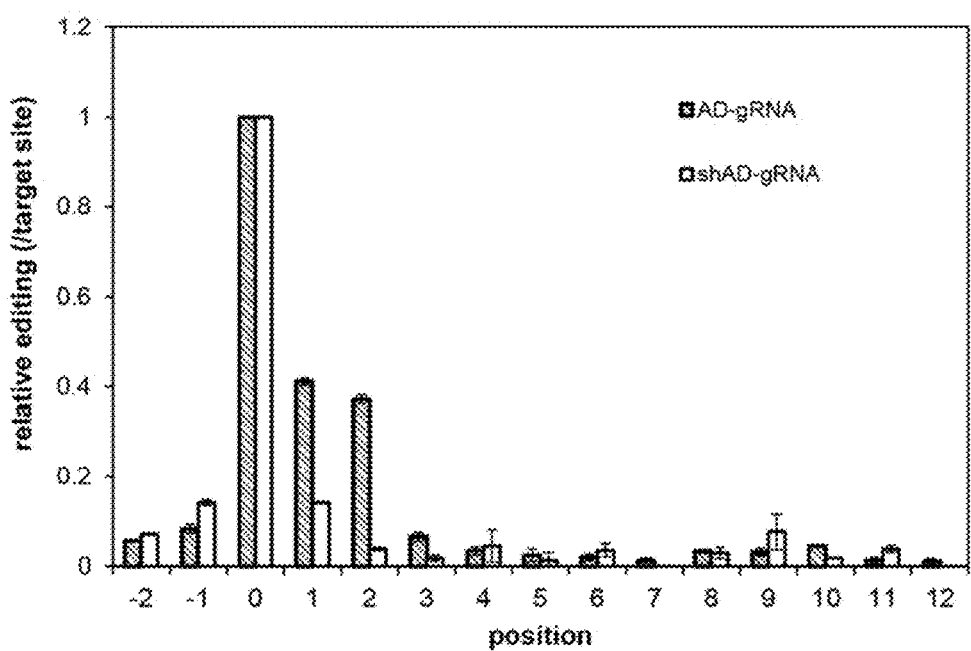
FIG. 9 is a view showing specificity of editing positions of the target editing guide RNAs.

Target editing guide RNAs (shAD-gRNA and AD-gRNA) were designed and synthesized according to the sequences of the respective target RNAs. The ARR in shAD-gRNA is of the 14-residue short-chain type identical to the ARR in the target editing guide RNA of Example 3 (SEQ ID NO: 18). AD-gRNA is a comparative example and has the ARR of 49 residues identical to the ARR of SL49 (SEQ ID NO: 29). Table 17 shows the sequences of shAD-gRNA with the ASR (first oligonucleotide) recognizing the target RNA underlined. The acquired target editing guide RNAs were evaluated for editing-inducing activity in the same manner as Evaluation 1 described above and were subjected to in vitro editing analysis. An editing percentage at each site was calculated to obtain a relative editing ratio (Aoff-target/Atarget) of the editing target A and the off-target site. The results are shown in FIG. 9.

TABLE 17

| | | |
|---|---|---|
| shAD-gRNA -2, 2 | GGGAAGCACUGCACGAUACAU AGGGUGUUCGCACCU | SEQ ID NO: 87 |
| shAD-gRNA -1, 1 | GGGAAGCACUGCACGCCUCUG CGGGUGUUCGCACCU | SEQ ID NO: 88 |
| shAD-gRNA 3.8 | GGGACGCCCGUACGGUAGCAA CGGGUGUUCGCACCU | SEQ ID NO: 89 |

TABLE 17-continued

| | | |
|---|---|---|
| shAD-gRNA 4.9 | GGGACGCCGUACGGUACGCAA CGGGUGUUCGCACCU | SEQ ID NO: 90 |
| shAD-gRNA 5.10 | GGGACGCGUACGGUACCGCAA CGGGUGUUCGCACCU | SEQ ID NO: 91 |
| shAD-gRNA 6.11 | GGGACGGUACGGUACCCGCAA CGGGUGUUCGCACCU | SEQ ID NO: 92 |
| shAD-gRNA 7.12 | GGGACGUACGGUACCCGGCAA CGGGUGUUCGCACCU | SEQ ID NO: 93 |

From FIG. 9, it can be seen that the target editing guide RNA (shAD-gRNA) with the short-chain ARR (second oligonucleotide) having 14 residues has higher editing position selectivity as compared to the target editing guide RNA (AD-gRNA) with the ARR having 49 residues.

The disclosures of Japanese Patent Application Nos. 2017-234341 (filed on Dec. 6, 2017) and 2018-151775 (filed on Aug. 10, 2018) are hereby incorporated by reference in its entirety. All the documents, patent applications, and technical standards described in this description are hereby incorporated by reference to the same extent as if each of the documents, patent applications, and technical standards is specifically and individually described as being incorporated by reference.

The invention claimed is:

1. An oligonucleotide for inducing site-specific editing of a target RNA, the oligonucleotide comprising:
   a first oligonucleotide identifying the target RNA; and
   a second oligonucleotide linked to the 3' side of the first oligonucleotide,
   wherein the first oligonucleotide is composed of
      a target-corresponding nucleotide residue corresponding to an adenosine residue in the target RNA,
      an oligonucleotide of 15 to 30 residues linked to the 5' side of the target-corresponding nucleotide residue and having a base sequence complementary to the target RNA,
      an oligonucleotide of 3 or 4 residues linked to the 3' side of the target-corresponding nucleotide residue and having a base sequence complementary to the target RNA,
   wherein the second oligonucleotide is composed of 2 to 24 nucleotide residues, the second oligonucleotide consists of a base sequence non-complementary to a base sequence corresponding to the target RNA, the second oligonucleotide has a base sequence capable of forming a stem-loop structure, and the second oligonucleotide contains a base sequence composed of consecutive guanine, uracil, and guanine in a region linked to a loop portion of the 5'-side stem portion and contains a base sequence capable of forming a complementary pair therewith in the 3'-side stem portion.

2. The oligonucleotide according to claim 1, wherein the second oligonucleotide contains a guanosine residue, or a derivative thereof, adjacently linked to the first oligonucleotide.

3. The oligonucleotide according to claim 1, wherein the target-corresponding nucleotide residue is a cytidine residue, a uridine residue, an adenosine residue, or a derivative thereof.

4. The oligonucleotide according to claim 1, wherein the site-specific editing is caused by an enzymatic reaction of adenosine deaminase.

5. A target RNA site-specific editing method comprising: bringing the oligonucleotide according to claim 1 into contact with a target RNA in the presence of adenosine deaminase.

6. The editing method according to claim 5, wherein the method is performed in a eukaryotic cell.

* * * * *

SEQUENCE LISTING

<160> NUMBER OF SEQ ID NOS: 97

<210> SEQ ID NO 1
<211> LENGTH: 40
<212> TYPE: DNA
<213> ORGANISM: Artificial
<220> FEATURE:
<223> OTHER INFORMATION: primer F

<400> SEQUENCE: 1
ctaatacgac tcactatagg gtgaatggcc acaagttcag          40

<210> SEQ ID NO 2
<211> LENGTH: 20
<212> TYPE: DNA
<213> ORGANISM: Artificial
<220> FEATURE:
<223> OTHER INFORMATION: primer R

```
<400> SEQUENCE: 2
tagcgtgaga agcactgcac                                                  20

<210> SEQ ID NO 3
<211> LENGTH: 178
<212> TYPE: DNA
<213> ORGANISM: Unknown
<220> FEATURE:
<223> OTHER INFORMATION: partial sequence from GFP

<400> SEQUENCE: 3
ctaatacgac tcactatagg gtgaatggcc acaagttcag cgtgagcggc gagggcgagg      60
gcgatgccac ctacggcaag ctgaccctga agttcatctg caccaccggc aagctgcctg    120
tgccctggcc caccctggtg accaccctga gctacggcgt gcagtgcttc tcacgcta      178

<210> SEQ ID NO 4
<211> LENGTH: 64
<212> TYPE: DNA
<213> ORGANISM: Artificial Sequence
<220> FEATURE:
<223> OTHER INFORMATION: primer R

<400> SEQUENCE: 4
aggtgggata cgaatattcc acccgctgcg gcgtgcagtg cttccctata gtgagtcgta     60
ttag                                                                  64

<210> SEQ ID NO 5
<211> LENGTH: 56
<212> TYPE: DNA
<213> ORGANISM: Artificial Sequence
<220> FEATURE:
<223> OTHER INFORMATION: primer R

<400> SEQUENCE: 5
aggtggcgaa ccacccgctg cggcgtgcag tgcttcccta gtgagtcg tattag            56

<210> SEQ ID NO 6
<211> LENGTH: 54
<212> TYPE: DNA
<213> ORGANISM: Artificial Sequence
<220> FEATURE:
<223> OTHER INFORMATION: primer R

<400> SEQUENCE: 6
aggtgcgaac acccgctgcg gcgtgcagtg cttccctata gtgagtcgta ttag            54

<210> SEQ ID NO 7
<211> LENGTH: 52
<212> TYPE: DNA
<213> ORGANISM: Artificial Sequence
<220> FEATURE:
<223> OTHER INFORMATION: primer R

<400> SEQUENCE: 7
aggtcgaaac ccgctgcggc gtgcagtgct tccctatagt gagtcgtatt ag              52

<210> SEQ ID NO 8
<211> LENGTH: 48
<212> TYPE: DNA
<213> ORGANISM: Artificial Sequence
<220> FEATURE:
<223> OTHER INFORMATION: primer R
```

<400> SEQUENCE: 8
agcgaaccgc tgcggcgtgc agtgcttccc tatagtgagt cgtattag        48

<210> SEQ ID NO 9
<211> LENGTH: 42
<212> TYPE: DNA
<213> ORGANISM: Artificial Sequence
<220> FEATURE:
<223> OTHER INFORMATION: primer R

<400> SEQUENCE: 9
ccgctgcggc gtgcagtgct tccctatagt gagtcgtatt ag        42

<210> SEQ ID NO 10
<211> LENGTH: 43
<212> TYPE: DNA
<213> ORGANISM: Artificial Sequence
<220> FEATURE:
<223> OTHER INFORMATION: primer R

<400> SEQUENCE: 10
cccgctgcgg cgtgcagtgc ttccctatag tgagtcgtat tag        43

<210> SEQ ID NO 11
<211> LENGTH: 42
<212> TYPE: DNA
<213> ORGANISM: Artificial Sequence
<220> FEATURE:
<223> OTHER INFORMATION: primer R

<400> SEQUENCE: 11
gagctgcggc gtgcagtgct tccctatagt gagtcgtatt ag        42

<210> SEQ ID NO 12
<211> LENGTH: 42
<212> TYPE: DNA
<213> ORGANISM: Artificial Sequence
<220> FEATURE:
<223> OTHER INFORMATION: primer R

<400> SEQUENCE: 12
cggctgcggc gtgcagtgct tccctatagt gagtcgtatt ag        42

<210> SEQ ID NO 13
<211> LENGTH: 40
<212> TYPE: DNA
<213> ORGANISM: Artificial Sequence
<220> FEATURE:
<223> OTHER INFORMATION: primer R

<400> SEQUENCE: 13
gctgcggcgt gcagtgcttc cctatagtga gtcgtattag        40

<210> SEQ ID NO 14
<211> LENGTH: 41
<212> TYPE: DNA
<213> ORGANISM: Artificial Sequence
<220> FEATURE:
<223> OTHER INFORMATION: primer R

<400> SEQUENCE: 14
cgctgcggcg tgcagtgctt ccctatagtg agtcgtatta g        41

<210> SEQ ID NO 15
<211> LENGTH: 21

<210> SEQ ID NO 15
<211> LENGTH: 21
<212> TYPE: DNA
<213> ORGANISM: Artificial Sequence
<220> FEATURE:
<223> OTHER INFORMATION: primer F

<400> SEQUENCE: 15
ctaatacgac tcactatagg g                                              21

<210> SEQ ID NO 16
<211> LENGTH: 46
<212> TYPE: RNA
<213> ORGANISM: Artificial Sequence
<220> FEATURE:
<223> OTHER INFORMATION: gRNA

<400> SEQUENCE: 16
gggaagcacu gcacgccgca gcgggugguu uauucguauc ccaccu                   46

<210> SEQ ID NO 17
<211> LENGTH: 38
<212> TYPE: RNA
<213> ORGANISM: Artificial Sequence
<220> FEATURE:
<223> OTHER INFORMATION: gRNA

<400> SEQUENCE: 17
gggaagcacu gcacgccgca gcgggugguu cgccaccu                            38

<210> SEQ ID NO 18
<211> LENGTH: 36
<212> TYPE: RNA
<213> ORGANISM: Artificial Sequence
<220> FEATURE:
<223> OTHER INFORMATION: gRNA

<400> SEQUENCE: 18
gggaagcacu gcacgccgca gcgggguguuc gcaccu                             36

<210> SEQ ID NO 19
<211> LENGTH: 34
<212> TYPE: RNA
<213> ORGANISM: Artificial Sequence
<220> FEATURE:
<223> OTHER INFORMATION: gRNA

<400> SEQUENCE: 19
gggaagcacu gcacgccgca gcggguuucg accu                                34

<210> SEQ ID NO 20
<211> LENGTH: 30
<212> TYPE: RNA
<213> ORGANISM: Artificial Sequence
<220> FEATURE:
<223> OTHER INFORMATION: gRNA

<400> SEQUENCE: 20
gggaagcacu gcacgccgca gcgguucgcu                                     30

<210> SEQ ID NO 21
<211> LENGTH: 24
<212> TYPE: RNA
<213> ORGANISM: Artificial Sequence
<220> FEATURE:
<223> OTHER INFORMATION: gRNA

<400> SEQUENCE: 21

```
ggaagcacu gcacgccgca gcgg                                           24

<210> SEQ ID NO 22
<211> LENGTH: 25
<212> TYPE: RNA
<213> ORGANISM: Artificial Sequence
<220> FEATURE:
<223> OTHER INFORMATION: gRNA

<400> SEQUENCE: 22
gggaagcacu gcacgccgca gcggg                                         25

<210> SEQ ID NO 23
<211> LENGTH: 24
<212> TYPE: RNA
<213> ORGANISM: Artificial Sequence
<220> FEATURE:
<223> OTHER INFORMATION: gRNA

<400> SEQUENCE: 23
gggaagcacu gcacgccgca gcuc                                          24

<210> SEQ ID NO 24
<211> LENGTH: 24
<212> TYPE: RNA
<213> ORGANISM: Artificial Sequence
<220> FEATURE:
<223> OTHER INFORMATION: gRNA

<400> SEQUENCE: 24
gggaagcacu gcacgccgca gccg                                          24

<210> SEQ ID NO 25
<211> LENGTH: 22
<212> TYPE: RNA
<213> ORGANISM: Artificial Sequence
<220> FEATURE:
<223> OTHER INFORMATION: gRNA

<400> SEQUENCE: 25
gggaagcacu gcacgccgca gc                                            22

<210> SEQ ID NO 26
<211> LENGTH: 23
<212> TYPE: RNA
<213> ORGANISM: Artificial Sequence
<220> FEATURE:
<223> OTHER INFORMATION: gRNA

<400> SEQUENCE: 26
gggaagcacu gcacgccgca gcg                                           23

<210> SEQ ID NO 27
<211> LENGTH: 51
<212> TYPE: DNA
<213> ORGANISM: Artificial Sequence
<220> FEATURE:
<223> OTHER INFORMATION: primer F

<400> SEQUENCE: 27
ctaatacgac tcactatagg gaagcactgc acgccgcagc gggtggaata g            51

<210> SEQ ID NO 28
<211> LENGTH: 49
<212> TYPE: DNA
<213> ORGANISM: Artificial Sequence
```

```
<220> FEATURE:
<223> OTHER INFORMATION: primer R

<400> SEQUENCE: 28
aggtgggata ctataacaac atttagcata ttgttatact attccaccc          49

<210> SEQ ID NO 29
<211> LENGTH: 72
<212> TYPE: RNA
<213> ORGANISM: Artificial Sequence
<220> FEATURE:
<223> OTHER INFORMATION: gRNA

<400> SEQUENCE: 29
gggaagcacu gcacgccgca gccgggugga auaguauaac aauaugcuaa auguuguuau   60 aguauoccac cu                                                      72

<210> SEQ ID NO 30
<211> LENGTH: 26
<212> TYPE: DNA
<213> ORGANISM: Artificial Sequence
<220> FEATURE:
<223> OTHER INFORMATION: primer F

<400> SEQUENCE: 30
gcatgctcga ggggccgatg gtgagc                                    26

<210> SEQ ID NO 31
<211> LENGTH: 21
<212> TYPE: DNA
<213> ORGANISM: Artificial Sequence
<220> FEATURE:
<223> OTHER INFORMATION: primer R

<400> SEQUENCE: 31
cagggtgggc tagggcacag g                                         21

<210> SEQ ID NO 32
<211> LENGTH: 21
<212> TYPE: DNA
<213> ORGANISM: Artificial Sequence
<220> FEATURE:
<223> OTHER INFORMATION: primer F

<400> SEQUENCE: 32
cctgtgccct agcccaccct g                                         21

<210> SEQ ID NO 33
<211> LENGTH: 31
<212> TYPE: DNA
<213> ORGANISM: Artificial Sequence
<220> FEATURE:
<223> OTHER INFORMATION: primer R

<400> SEQUENCE: 33
ggtacaagct ttcacttgta cagctcatcc a                              31

<210> SEQ ID NO 34
<211> LENGTH: 19
<212> TYPE: DNA
<213> ORGANISM: Artificial Sequence
<220> FEATURE:
<223> OTHER INFORMATION: primer F

<400> SEQUENCE: 34
```
tggcaccaaa atcaacggg                                              19

<210> SEQ ID NO 35
<211> LENGTH: 22
<212> TYPE: DNA
<213> ORGANISM: Artificial Sequence
<220> FEATURE:
<223> OTHER INFORMATION: primer R

<400> SEQUENCE: 35
gctattgtct tcccaatcct cc                                          22

<210> SEQ ID NO 36
<211> LENGTH: 37
<212> TYPE: DNA
<213> ORGANISM: Artificial Sequence
<220> FEATURE:
<223> OTHER INFORMATION: primer F

<400> SEQUENCE: 36
ctaagatctg tcaccagggt gggccagggg gtggttc                          37

<210> SEQ ID NO 37
<211> LENGTH: 37
<212> TYPE: DNA
<213> ORGANISM: Artificial Sequence
<220> FEATURE:
<223> OTHER INFORMATION: primer R

<400> SEQUENCE: 37
ctaaagctta aaaggtggc gaaccacccc ctggccc                           37

<210> SEQ ID NO 38
<211> LENGTH: 22
<212> TYPE: DNA
<213> ORGANISM: Artificial Sequence
<220> FEATURE:
<223> OTHER INFORMATION: primer F

<400> SEQUENCE: 38
ctgggaaatc accataaacg tg                                          22

<210> SEQ ID NO 39
<211> LENGTH: 21
<212> TYPE: DNA
<213> ORGANISM: Artificial Sequence
<220> FEATURE:
<223> OTHER INFORMATION: primer R

<400> SEQUENCE: 39
cagctatgac catgattacg c                                           21

<210> SEQ ID NO 40
<211> LENGTH: 38
<212> TYPE: DNA
<213> ORGANISM: Artificial Sequence
<220> FEATURE:
<223> OTHER INFORMATION: primer F

<400> SEQUENCE: 40
ctaagatctg tcaccagggt gggccagggg gtgttcgc                         38

<210> SEQ ID NO 41
<211> LENGTH: 35
<212> TYPE: DNA
<213> ORGANISM: Artificial Sequence

```
<220> FEATURE:
<223> OTHER INFORMATION: primer R

<400> SEQUENCE: 41
ctaaagctta aaaaggtgcg aacacccct ggccc                          35

<210> SEQ ID NO 42
<211> LENGTH: 46
<212> TYPE: DNA
<213> ORGANISM: Artificial Sequence
<220> FEATURE:
<223> OTHER INFORMATION: primer F

<400> SEQUENCE: 42
gctatagatc tgtcaccagg gtgggccagg gggtggaata gtatac             46

<210> SEQ ID NO 43
<211> LENGTH: 55
<212> TYPE: DNA
<213> ORGANISM: Artificial Sequence
<220> FEATURE:
<223> OTHER INFORMATION: primer R

<400> SEQUENCE: 43
ccgataagct taaaaggtg ggatactata ccacgaatgg tatactattc caccc    55

<210> SEQ ID NO 44
<211> LENGTH: 27
<212> TYPE: DNA
<213> ORGANISM: Artificial Sequence
<220> FEATURE:
<223> OTHER INFORMATION: primer R

<400> SEQUENCE: 44
gctctagaac catgggggt tctcatc                                   27

<210> SEQ ID NO 45
<211> LENGTH: 25
<212> TYPE: DNA
<213> ORGANISM: Artificial Sequence
<220> FEATURE:
<223> OTHER INFORMATION: primer F

<400> SEQUENCE: 45
gatggtacct cagggcgtga gtgag                                    25

<210> SEQ ID NO 46
<211> LENGTH: 22
<212> TYPE: DNA
<213> ORGANISM: Artificial Sequence
<220> FEATURE:
<223> OTHER INFORMATION: primer

<400> SEQUENCE: 46
ctaatacgac tccactatag gg                                       22

<210> SEQ ID NO 47
<211> LENGTH: 18
<212> TYPE: DNA
<213> ORGANISM: Artificial Sequence
<220> FEATURE:
<223> OTHER INFORMATION: primer R

<400> SEQUENCE: 47
tagaaggcac agtcgagg                                            18
```

```
<210> SEQ ID NO 48
<211> LENGTH: 20
<212> TYPE: DNA
<213> ORGANISM: Artificial Sequence
<220> FEATURE:
<223> OTHER INFORMATION: primer F

<400> SEQUENCE: 48
gacctcagct tgtctgcttc                                               20

<210> SEQ ID NO 49
<211> LENGTH: 24
<212> TYPE: RNA
<213> ORGANISM: Artificial Sequence
<220> FEATURE:
<223> OTHER INFORMATION: ARR

<400> SEQUENCE: 49
ggguggaaua uucguauccc accu                                          24

<210> SEQ ID NO 50
<211> LENGTH: 16
<212> TYPE: RNA
<213> ORGANISM: Artificial Sequence
<220> FEATURE:
<223> OTHER INFORMATION: ARR

<400> SEQUENCE: 50
gggugguucg ccaccu                                                   16

<210> SEQ ID NO 51
<211> LENGTH: 14
<212> TYPE: RNA
<213> ORGANISM: Artificial Sequence
<220> FEATURE:
<223> OTHER INFORMATION: ARR

<400> SEQUENCE: 51
ggguguucgc accu                                                     14

<210> SEQ ID NO 52
<211> LENGTH: 12
<212> TYPE: RNA
<213> ORGANISM: Artificial Sequence
<220> FEATURE:
<223> OTHER INFORMATION: ARR

<400> SEQUENCE: 52
ggguuucgac cu                                                       12

<210> SEQ ID NO 53
<211> LENGTH: 14
<212> TYPE: RNA
<213> ORGANISM: Artificial Sequence
<220> FEATURE:
<223> OTHER INFORMATION: ARR

<400> SEQUENCE: 53
ggguggaaac accu                                                     14

<210> SEQ ID NO 54
<211> LENGTH: 14
<212> TYPE: RNA
<213> ORGANISM: Artificial Sequence
<220> FEATURE:
<223> OTHER INFORMATION: ARR
```

```
<400> SEQUENCE: 54
ggguggaaac accc                                                      14

<210> SEQ ID NO 55
<211> LENGTH: 14
<212> TYPE: RNA
<213> ORGANISM: Artificial Sequence
<220> FEATURE:
<223> OTHER INFORMATION: ARR

<400> SEQUENCE: 55
uucacgaaag ugaa                                                      14

<210> SEQ ID NO 56
<211> LENGTH: 14
<212> TYPE: RNA
<213> ORGANISM: Artificial Sequence
<220> FEATURE:
<223> OTHER INFORMATION: ARR

<400> SEQUENCE: 56
ugguggaaac acca                                                      14

<210> SEQ ID NO 57
<211> LENGTH: 14
<212> TYPE: RNA
<213> ORGANISM: Artificial Sequence
<220> FEATURE:
<223> OTHER INFORMATION: ARR

<400> SEQUENCE: 57
guguggaaac acac                                                      14

<210> SEQ ID NO 58
<211> LENGTH: 14
<212> TYPE: RNA
<213> ORGANISM: Artificial Sequence
<220> FEATURE:
<223> OTHER INFORMATION: ARR

<400> SEQUENCE: 58
ggcuggaaac agcc                                                      14

<210> SEQ ID NO 59
<211> LENGTH: 14
<212> TYPE: RNA
<213> ORGANISM: Artificial Sequence
<220> FEATURE:
<223> OTHER INFORMATION: ARR

<400> SEQUENCE: 59
gggaggaaac uccc                                                      14

<210> SEQ ID NO 60
<211> LENGTH: 14
<212> TYPE: RNA
<213> ORGANISM: Artificial Sequence
<220> FEATURE:
<223> OTHER INFORMATION: ARR

<400> SEQUENCE: 60
gggucgaaag accc                                                      14

<210> SEQ ID NO 61
```

```
<211> LENGTH: 14
<212> TYPE: RNA
<213> ORGANISM: Artificial Sequence
<220> FEATURE:
<223> OTHER INFORMATION: ARR

<400> SEQUENCE: 61
uuguggaaac acaa                                                     14

<210> SEQ ID NO 62
<211> LENGTH: 14
<212> TYPE: RNA
<213> ORGANISM: Artificial Sequence
<220> FEATURE:
<223> OTHER INFORMATION: ARR

<400> SEQUENCE: 62
ggcaggaaac ugcc                                                     14

<210> SEQ ID NO 63
<211> LENGTH: 14
<212> TYPE: RNA
<213> ORGANISM: Artificial Sequence
<220> FEATURE:
<223> OTHER INFORMATION: ARR

<400> SEQUENCE: 63
ggcacgaaag ugcc                                                     14

<210> SEQ ID NO 64
<211> LENGTH: 40
<212> TYPE: DNA
<213> ORGANISM: Artificial Sequence
<220> FEATURE:
<223> OTHER INFORMATION: primer_F

<400> SEQUENCE: 64
ctaatacgac tcactatagg gtgaatggcc acaagttcag                          40

<210> SEQ ID NO 65
<211> LENGTH: 20
<212> TYPE: DNA
<213> ORGANISM: Artificial Sequence
<220> FEATURE:
<223> OTHER INFORMATION: Primner_R

<400> SEQUENCE: 65
tagcgtgaga agcactgcac                                               20

<210> SEQ ID NO 66
<211> LENGTH: 14
<212> TYPE: RNA
<213> ORGANISM: Artificial Sequence
<220> FEATURE:
<223> OTHER INFORMATION: ARR

<400> SEQUENCE: 66
ggguguucgc accu                                                     14

<210> SEQ ID NO 67
<211> LENGTH: 39
<212> TYPE: RNA
<213> ORGANISM: Artificial Sequence
<220> FEATURE:
<223> OTHER INFORMATION: gRNA

<400> SEQUENCE: 67
```

```
gaagguucag cagcucgaac caaggggugu ucgcaccuu                              39
```

<210> SEQ ID NO 68
<211> LENGTH: 24
<212> TYPE: RNA
<213> ORGANISM: Artificial Sequence
<220> FEATURE:
<223> OTHER INFORMATION: ASR

<400> SEQUENCE: 68

```
gaagguucag cagcucgaac caag                                             24
```

<210> SEQ ID NO 69
<211> LENGTH: 936
<212> TYPE: RNA
<213> ORGANISM: Artificial Sequence
<220> FEATURE:
<223> OTHER INFORMATION: Rluc

<400> SEQUENCE: 69

```
auggcuucca aggaguacga ccccgagcaa cgcaaacgca ugaucacugg gccucagugg       60
ugggcucgcu gcaagcaaau gaacgugcug gacuccuuca ucaacuacua ugauccgag      120
aggcacgccg agaacgccgu gauuuuucug cauggguaacg cugccuccag cuaccugugg    180
aggcacgucg ugccuacau cgagcccgug gcuagaugca ucaucccuga ucugaucgga      240
auggguaagu ccggcaagag cgggaauggc ucauaucgcc uccuggauca cuacaaguac     300
cucaccgcuu aguucgagcu gcugaaccuu ccaaagaaaa ucaucuuugu gggccacgac    360
uggggggcuu gucuggccuu ucacuacucc uacgagcacc aagacaagau caaggccauc   420
guccaugcug agagugcugu ggacgugauc gaguccuggg acgaguggcc ugacaucgag   480
gaggauaucg cccugaucaa gagcgaagag ggcgagaaaa uggugcuuga gaauaacuuc  540
uucgucgaga ccaugcuccc aagcaagauc augcggaaac uggagccuga ggaguucgcu  600
gccuaccugg agccauucaa ggagaagggc gagguuagac ggccuacccu cuccuggccu  660
cgcgagaucc cucucguuaa gggaggcaag cccgacgucg uccagauugu ccgcaacuac  720
aacgccuacc uucgggccag cgacgaucug ccuaagaugu caucgaguc cgacccuggg  780
uucuuuucca acgcuauugu cgagggagcu aagaaguucc cuaacaccga guucgugaag  840
gugaagggcc uccacuucag ccaggaggac gcuccagaug aaaugggua guacaucaag   900
agcuucgugg agcgcgugcu gaagaacgag caguaa                              936
```

<210> SEQ ID NO 70
<211> LENGTH: 71
<212> TYPE: RNA
<213> ORGANISM: Artificial Sequence
<220> FEATURE:
<223> OTHER INFORMATION: gRNA

<400> SEQUENCE: 70

```
ggguggaaua guauaacaau augcuaaaug uuguuauagu aucccaccug cgcaggcgug       60
cagugcuucu c                                                          71
```

<210> SEQ ID NO 71
<211> LENGTH: 62
<212> TYPE: RNA
<213> ORGANISM: Artificial Sequence
<220> FEATURE:
<223> OTHER INFORMATION: gRNA

<400> SEQUENCE: 71 gggguggaaua guauaccauu cgugguauag uaucccaccu gcgcaggcgu gcagugcuuc      60
uc                                                                    62

<210> SEQ ID NO 72
<211> LENGTH: 56
<212> TYPE: RNA
<213> ORGANISM: Artificial Sequence
<220> FEATURE:
<223> OTHER INFORMATION: gRNA

<400> SEQUENCE: 72
ggguggaaua guauauucgu auaguauccc accugcgcag gcgugcagug cuucuc          56

<210> SEQ ID NO 73
<211> LENGTH: 43
<212> TYPE: RNA
<213> ORGANISM: Artificial Sequence
<220> FEATURE:
<223> OTHER INFORMATION: gRNA

<400> SEQUENCE: 73
ggguggaaua uucguauccc accugcgcag gcgugcagug cuu                       43

<210> SEQ ID NO 74
<211> LENGTH: 35
<212> TYPE: RNA
<213> ORGANISM: Artificial Sequence
<220> FEATURE:
<223> OTHER INFORMATION: gRNA

<400> SEQUENCE: 74
gggugguucg ccaccugcgc aggcgugcag ugcuu                                35

<210> SEQ ID NO 75
<211> LENGTH: 33
<212> TYPE: RNA
<213> ORGANISM: Artificial Sequence
<220> FEATURE:
<223> OTHER INFORMATION: gRNA

<400> SEQUENCE: 75
ggguguucgc accugcgcag gcgugcagug cuu                                  33

<210> SEQ ID NO 76
<211> LENGTH: 31
<212> TYPE: RNA
<213> ORGANISM: Artificial Sequence
<220> FEATURE:
<223> OTHER INFORMATION: gRNA

<400> SEQUENCE: 76
ggguuucgac cugcgcaggc gugcagugcu u                                    31

<210> SEQ ID NO 77
<211> LENGTH: 28
<212> TYPE: RNA
<213> ORGANISM: Artificial Sequence
<220> FEATURE:
<223> OTHER INFORMATION: gRNA

<400> SEQUENCE: 77
ggguucgcug cgcaggcgug cagugcuu                                        28

```
<210> SEQ ID NO 78
<211> LENGTH: 62
<212> TYPE: RNA
<213> ORGANISM: Artificial Sequence
<220> FEATURE:
<223> OTHER INFORMATION: gRNA

<400> SEQUENCE: 78
gggaagcacu gcacgccgca gcggguggaa uaguauacca uucgugguau aguaucccac      60
cu                                                                    62

<210> SEQ ID NO 79
<211> LENGTH: 56
<212> TYPE: RNA
<213> ORGANISM: Artificial Sequence
<220> FEATURE:
<223> OTHER INFORMATION: gRNA

<400> SEQUENCE: 79
gggaagcacu gcacgccgca gcggguggaa uaguauauuc guauaguauc ccaccu          56

<210> SEQ ID NO 80
<211> LENGTH: 154
<212> TYPE: RNA
<213> ORGANISM: Artificial Sequence
<220> FEATURE:
<223> OTHER INFORMATION: sGFP_modified

<400> SEQUENCE: 80
gggugaaugg ccacaaguuc agcgugagcg gcgagggcga gggcgaugcc accuacggca      60
agcugacccu gaaguucauc ugcaccaccg gcaagcugcc ugugcccugg cccacccugg     120
ugaccacccu gagcaaaggc gugcagugcu ucuc                                 154

<210> SEQ ID NO 81
<211> LENGTH: 160
<212> TYPE: RNA
<213> ORGANISM: Artificial Sequence
<220> FEATURE:
<223> OTHER INFORMATION: sGFP_modified

<400> SEQUENCE: 81
gggugaaugg ccacaaguuc agcgugagcg gcgagggcga gggcgaugcc accuacggca      60
agcugacccu gaaguucauc ugcaccaccg gcaagcugcc ugugcccugg cccacccugg     120
ugaccacccu gauauauauc gugcagugcu ucucacgcua                           160

<210> SEQ ID NO 82
<211> LENGTH: 204
<212> TYPE: RNA
<213> ORGANISM: Artificial Sequence
<220> FEATURE:
<223> OTHER INFORMATION: sGFP_modified

<400> SEQUENCE: 82
gggugaaugg ccacaaguuc agcgugagcg gcgagggcga gggcgaugcc accuacggca      60
agcugacccu gaaguucauc ugcaccaccg gcaagcugcc ugugcccugg cccacccugg     120
ugaccacccu gagcuacggc gugcagugcu ucucacgcua cgcuacguua cuaccguacg     180
ggcgugcuga agaacgagca guaa                                            204

<210> SEQ ID NO 83
<211> LENGTH: 204
<212> TYPE: RNA
```

```
<213> ORGANISM: Artificial Sequence
<220> FEATURE:
<223> OTHER INFORMATION: sGFP_modified

<400> SEQUENCE: 83
gggugaaugg ccacaaguuc agcgugagcg gcgagggcga gggcgaugcc accuacggca      60
agcugacccu gaaguucauc ugcaccaccg gcaagcugcc ugugcccugg cccacccugg     120
ugaccacccu gagcuacggc gugcagugcu ucucacgcua cgcuacguua cguaccguac    180
ggcgugcuga agaacgagca guaa                                            204

<210> SEQ ID NO 84
<211> LENGTH: 204
<212> TYPE: RNA
<213> ORGANISM: Artificial Sequence
<220> FEATURE:
<223> OTHER INFORMATION: sGFP_modified

<400> SEQUENCE: 84
gggugaaugg ccacaaguuc agcgugagcg gcgagggcga gggcgaugcc accuacggca      60
agcugacccu gaaguucauc ugcaccaccg gcaagcugcc ugugcccugg cccacccugg     120
ugaccacccu gagcuacggc gugcagugcu ucucacgcua cgcuacguua cgguaccgua    180
cgcgugcuga agaacgagca guaa                                            204

<210> SEQ ID NO 85
<211> LENGTH: 204
<212> TYPE: RNA
<213> ORGANISM: Artificial Sequence
<220> FEATURE:
<223> OTHER INFORMATION: sGFP_modified

<400> SEQUENCE: 85
gggugaaugg ccacaaguuc agcgugagcg gcgagggcga gggcgaugcc accuacggca      60
agcugacccu gaaguucauc ugcaccaccg gcaagcugcc ugugcccugg cccacccugg     120
ugaccacccu gagcuacggc gugcagugcu ucucacgcua cgcuacguua cggguaccgu    180
accgugcuga agaacgagca guaa                                            204

<210> SEQ ID NO 86
<211> LENGTH: 204
<212> TYPE: RNA
<213> ORGANISM: Artificial Sequence
<220> FEATURE:
<223> OTHER INFORMATION: sGFP_modified

<400> SEQUENCE: 86
gggugaaugg ccacaaguuc agcgugagcg gcgagggcga gggcgaugcc accuacggca      60
agcugacccu gaaguucauc ugcaccaccg gcaagcugcc ugugcccugg cccacccugg     120
ugaccacccu gagcuacggc gugcagugcu ucucacgcua cgcuacguua ccggguaccg    180
uacgugcuga agaacgagca guaa                                            204

<210> SEQ ID NO 87
<211> LENGTH: 36
<212> TYPE: RNA
<213> ORGANISM: Artificial Sequence
<220> FEATURE:
<223> OTHER INFORMATION: gRNA

<400> SEQUENCE: 87
gggaagcacu gcacgauaca uaggguguuc gcaccu                                36
```

```
<210> SEQ ID NO 88
<211> LENGTH: 36
<212> TYPE: RNA
<213> ORGANISM: Artificial Sequence
<220> FEATURE:
<223> OTHER INFORMATION: gRNA

<400> SEQUENCE: 88
gggaagcacu gcacgccucu gcggguguuc gcaccu                                   36

<210> SEQ ID NO 89
<211> LENGTH: 36
<212> TYPE: RNA
<213> ORGANISM: Artificial Sequence
<220> FEATURE:
<223> OTHER INFORMATION: gRNA

<400> SEQUENCE: 89
gggacgcccg uacgguagca acggguguuc gcaccu                                   36

<210> SEQ ID NO 90
<211> LENGTH: 36
<212> TYPE: RNA
<213> ORGANISM: Artificial Sequence
<220> FEATURE:
<223> OTHER INFORMATION: gRNA

<400> SEQUENCE: 90
gggacgccgu acgguacgca acggguguuc gcaccu                                   36

<210> SEQ ID NO 91
<211> LENGTH: 36
<212> TYPE: RNA
<213> ORGANISM: Artificial Sequence
<220> FEATURE:
<223> OTHER INFORMATION: gRNA

<400> SEQUENCE: 91
gggacgcgua cgguaccgca acggguguuc gcaccu                                   36

<210> SEQ ID NO 92
<211> LENGTH: 36
<212> TYPE: RNA
<213> ORGANISM: Artificial Sequence
<220> FEATURE:
<223> OTHER INFORMATION: gRNA

<400> SEQUENCE: 92
gggacgguac gguacccgca acggguguuc gcaccu                                   36

<210> SEQ ID NO 93
<211> LENGTH: 36
<212> TYPE: RNA
<213> ORGANISM: Artificial Sequence
<220> FEATURE:
<223> OTHER INFORMATION: gRNA

<400> SEQUENCE: 93
gggacguacg guacccggca acggguguuc gcaccu                                   36

<210> SEQ ID NO 94
<211> LENGTH: 22
<212> TYPE: RNA
<213> ORGANISM: Artificial Sequence
<220> FEATURE:
```

```
<223> OTHER INFORMATION: gRNA model

<400> SEQUENCE: 94
gggaagcacu gcacgccgca gc                                          22

<210> SEQ ID NO 95
<211> LENGTH: 34
<212> TYPE: RNA
<213> ORGANISM: Artificial Sequence
<220> FEATURE:
<223> OTHER INFORMATION: Target model

<400> SEQUENCE: 95
cacccugagc uacggcgugc agugcuucuc acgc                             34

<210> SEQ ID NO 96
<211> LENGTH: 34
<212> TYPE: RNA
<213> ORGANISM: Artificial Sequence
<220> FEATURE:
<223> OTHER INFORMATION: rRNA model
<220> FEATURE:
<221> NAME/KEY: misc_feature
<222> LOCATION: (1)..(16)
<223> OTHER INFORMATION: n is a, c, g, or u
<220> FEATURE:
<221> NAME/KEY: misc_feature
<222> LOCATION: (18)..(22)
<223> OTHER INFORMATION: n is a, c, g, or u
<220> FEATURE:
<221> NAME/KEY: misc_feature
<222> LOCATION: (26)..(29)
<223> OTHER INFORMATION: n is a, c, g, or u
<220> FEATURE:
<221> NAME/KEY: misc_feature
<222> LOCATION: (33)..(34)
<223> OTHER INFORMATION: n is a, c, g, or u

<400> SEQUENCE: 96
nnnnnnnnnn nnnnnncnnn nngugnnnnc acnn                             34

<210> SEQ ID NO 97
<211> LENGTH: 20
<212> TYPE: RNA
<213> ORGANISM: Artificial Sequence
<220> FEATURE:
<223> OTHER INFORMATION: Target RNA model
<220> FEATURE:
<221> NAME/KEY: misc_feature
<222> LOCATION: (1)..(3)
<223> OTHER INFORMATION: n is a, c, g, or u
<220> FEATURE:
<221> NAME/KEY: misc_feature
<222> LOCATION: (5)..(20)
<223> OTHER INFORMATION: n is a, c, g, or u

<400> SEQUENCE: 97
nnnannnnnn nnnnnnnnnn                                             20
```